US011232365B2

(12) United States Patent
Sundararaman et al.

(10) Patent No.: US 11,232,365 B2
(45) Date of Patent: Jan. 25, 2022

(54) DIGITAL ASSISTANT PLATFORM

(71) Applicant: Accenture Global Solutions Limited, Dublin (IE)

(72) Inventors: Arun Sundararaman, Chennai (IN); Uday Kumar Ramamoorthy, Chenam (IN); Sureshkumar Pargunarajan, Chennai (IN); Sangeetha Appusamy, Chennai (IN); A. Deni Xavier Gladis, Pollachi (IN)

(73) Assignee: Accenture Global Solutions Limited, Dublin (IE)

( * ) Notice: Subject to any disclaimer, the term of this patent is extended or adjusted under 35 U.S.C. 154(b) by 52 days.

(21) Appl. No.: 16/659,968

(22) Filed: Oct. 22, 2019

(65) Prior Publication Data

US 2020/0050949 A1 Feb. 13, 2020

Related U.S. Application Data

(63) Continuation-in-part of application No. 16/008,602, filed on Jun. 14, 2018, now Pat. No. 10,810,223.

(51) Int. Cl.

| | |
|---|---|
| ***G06F 16/2452*** | (2019.01) |
| ***G06F 16/25*** | (2019.01) |
| ***G06F 16/242*** | (2019.01) |
| ***G06F 16/248*** | (2019.01) |
| ***G06F 40/284*** | (2020.01) |
| ***G06N 5/04*** | (2006.01) |

(Continued)

(52) U.S. Cl.

CPC ............ *G06N 5/04* (2013.01); *G06F 16/248* (2019.01); *G06F 16/2423* (2019.01); *G06F 16/24522* (2019.01); *G06F 16/252* (2019.01); *G06F 40/284* (2020.01); *G06N 20/00* (2019.01); *G16H 10/60* (2018.01)

(58) Field of Classification Search

CPC .......... G06N 5/04; G06N 20/00; G16H 10/60; G06F 16/24522; G06F 16/2423; G06F 16/248; G06F 16/252; G06F 40/284

See application file for complete search history.

(56) References Cited

U.S. PATENT DOCUMENTS

| | | | | |
|---|---|---|---|---|
| 8,745,096 B1 * | 6/2014 | Noble | .................. | G06F 16/951 707/811 |
| 10,467,261 B1 * | 11/2019 | Doyle | .................. | G06F 16/248 |
| 10,628,553 B1 * | 4/2020 | Murrish | .................. | G06F 19/32 |

(Continued)

*Primary Examiner* — Ken Hoang

(74) *Attorney, Agent, or Firm* — Harrity & Harrity, LLP

(57) ABSTRACT

A digital assistant platform may receive a query relating to a target data file. The target data file may be associated with a standardized data set. The standardized data set may include data files that are aggregated based on data elements associated with the data files, and may be configured to enable a plurality of services. The digital assistant platform may extract, based on the query, one or more keywords, and identify an intent classification and an entity associated with the query. The digital assistant platform may analyze the plurality of services to identify a target service to enable, and analyze the data elements to identify the target data file. The digital assistant platform may determine, using the target service, analytical information associated with a data element of the target data file, and generate a response to the query based on the analytical information.

20 Claims, 13 Drawing Sheets

500

Receive, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements — 502

Extract, based on the query, one or more keywords — 504

Identify, using a machine learning model, an intent classification associated with the query and an entity associated with the query, wherein the machine learning model is trained to identify the intent classification based on an association between the one or more keywords and the plurality of services, and wherein the machine learning model is trained to identify the entity based on an association between the one or more keywords and the plurality of data elements of the standardized data set — 506

Analyze, based on the intent classification, the plurality of services, to identify a target service to enable — 508

Analyze, based on the entity, the plurality of data elements of the standardized data set, to identify the target data file — 510

Determine, using the target service, analytical information associated with a data element of the target data file — 512

Generate a response to the query based on the analytical information — 514

(51) Int. Cl.
*G06N 20/00* (2019.01)
*G16H 10/60* (2018.01)

(56) References Cited

U.S. PATENT DOCUMENTS

| | | | | |
|---|---|---|---|---|
| 2007/0260492 | A1* | 11/2007 | Feied | G16H 10/60 705/3 |
| 2011/0119088 | A1* | 5/2011 | Gunn | G16H 40/67 705/3 |
| 2013/0332194 | A1* | 12/2013 | D'Auria | G16H 10/60 705/3 |
| 2015/0317337 | A1* | 11/2015 | Edgar | G06F 19/328 707/751 |
| 2016/0019357 | A1* | 1/2016 | Marzula | G06F 19/328 705/2 |
| 2018/0157721 | A1* | 6/2018 | Khaitan | G06F 16/3329 |
| 2018/0308473 | A1* | 10/2018 | Scholar | A63F 13/00 |
| 2020/0013124 | A1* | 1/2020 | Obee | G06N 20/00 |

* cited by examiner

100

DIGITAL ASSISTANT PLATFORM

RELATED APPLICATION

This application is a continuation-in-part (CIP) of U.S. patent application Ser. No. 16/008,602, filed on Jun. 14, 2018, and entitled "DATA PLATFORM FOR AUTOMATED DATA EXTRACTION, TRANSFORMATION, AND/OR LOADING," the content of which is incorporated by reference herein in its entirety.

BACKGROUND

As more and more industries become digitized, it is not uncommon for different kinds of information to be exchanged electronically. The healthcare industry is one in which an Electronic Data Interchange (EDI) plays a central role in facilitating the electronic communication and exchange of healthcare related data, including, for example, data pertaining to health insurance claims, health insurance enrollment, eligibility data, claims settlement, medical records, and/or the like. The Health Insurance Portability and Accountability Act (HIPAA) has led to standardized claims administration and automation in the healthcare industry by employing EDI messages to exchange data.

SUMMARY

According to some implementations, a method may include receiving, by a device and from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements; extracting, by the device and based on the query, one or more keywords; identifying, by the device and using a machine learning model, an intent classification associated with the query and an entity associated with the query, wherein the machine learning model is trained to identify the intent classification based on an association between the one or more keywords and the plurality of services, and wherein the machine learning model is trained to identify the entity based on an association between the one or more keywords and the plurality of data elements of the standardized data set; analyzing, by the device and based on the intent classification, the plurality of services, to identify a target service to enable; analyzing, by the device and based on the entity, the plurality of data elements of the standardized data set, to identify the target data file; determining, by the device and using the target service, analytical information associated with a data element of the target data file; and generating, by the device, a response to the query based on the analytical information.

According to some implementations, a device may include one or more memories, and one or more processors, communicatively coupled to the one or more memories, configured to receive, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements; identify an intent classification associated with the query and an entity associated with the query, wherein the intent classification is identified based on an association between one or more keywords of the query and the plurality of services, and wherein the entity is identified based on an association between the one or more keywords and the plurality of data elements of the standardized data set; analyze, based on the intent classification, the plurality of services to identify a target service to enable; analyze, based on the entity, the plurality of data elements of the standardized data set to identify the target data file; determine, using the target service, analytical information associated with a data element of the target data file; and cause an action to be performed in connection with the analytical information.

According to some implementations, a non-transitory computer-readable medium may store one or more instructions that, when executed by one or more processors, cause the one or more processors to receive, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements; extract, based on the query, one or more keywords; identify one or more of an intent classification associated with the query or an entity associated with the query; analyze, based on the intent classification, the plurality of services to identify a target service to enable; analyze, based on the entity, the plurality of data elements of the standardized data set to identify the target data file; determine, using the target service, analytical information associated with a data element of the target data file; and generate a response to the query based on the analytical information.

DETAILED DESCRIPTION

Figure 1A:
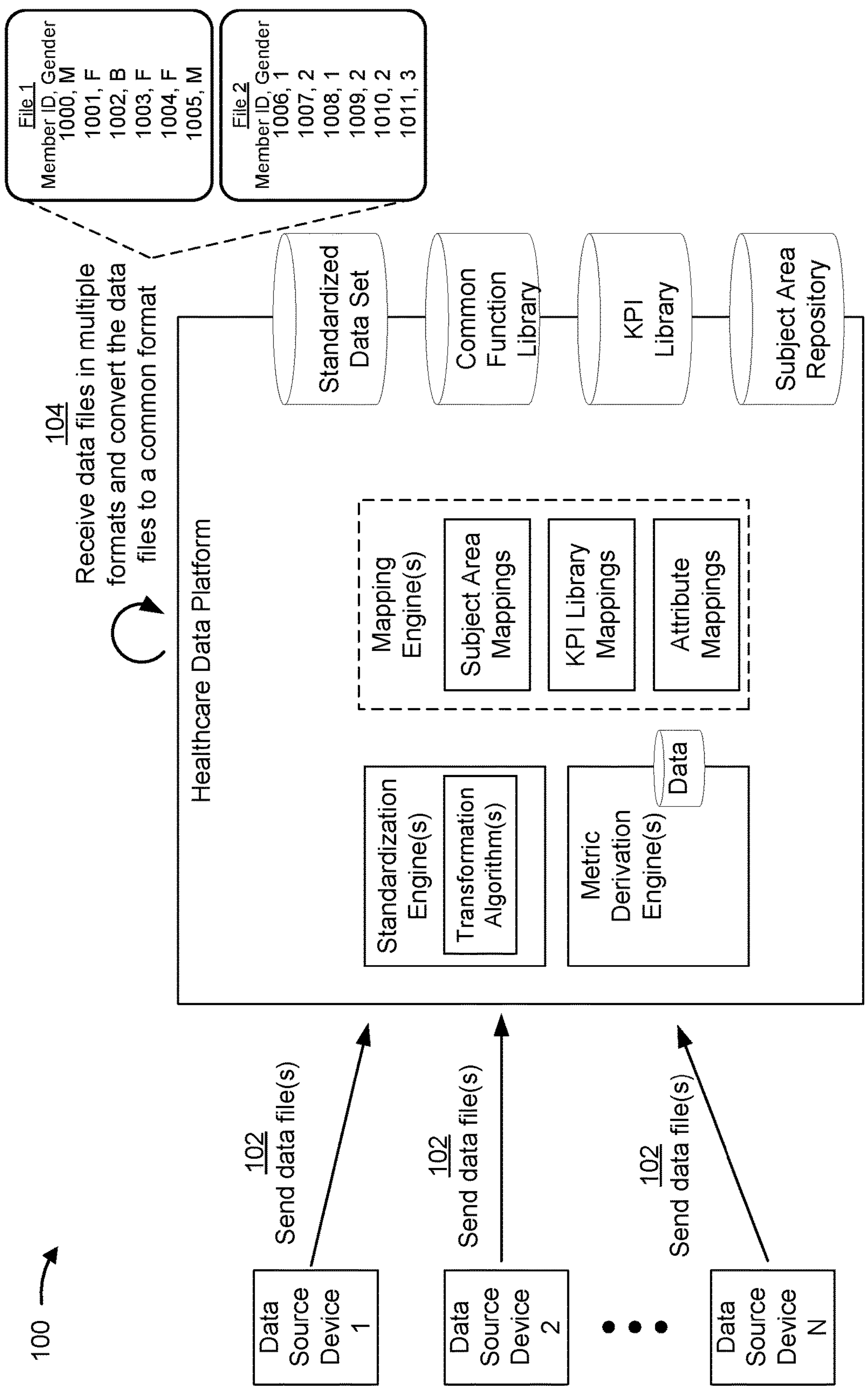
FIGS. 1A-1E are diagrams of an example implementation described herein.

The following detailed description of example implementations refers to the accompanying drawings. The same reference numbers in different drawings may identify the same or similar elements.

The healthcare industry is one of many industries that produces an enormous amount of data, including healthcare related data in forms of medical records, hospital records, primary care physician records, billing records, health insurance records (e.g., eligibility data, enrollment data, claims records, claims information, paid amounts, and/or declined amounts), and/or the like. The data may be transmitted, received, exchanged, and/or otherwise communicated by various entities in various formats using an electronic data interchange (EDI). The EDI facilitates secure, electronic exchange of data in a variety of standardized formats for use by various healthcare clients, such as healthcare professionals, healthcare institutions (e.g., hospitals, primary care physicians, and/or the like), insurance clients, and/or the like. The various healthcare clients may employ one or more data analytics tools to access and manipulate the enormous amount of data available from the EDI, for example, to assess trends, measure key performance indicators (KPIs), calculate metrics for driving decisions to deliver better medical care, calculate metrics for driving decisions to reduce waste, and/or the like.

The various entities that send, receive, exchange, and/or otherwise communicate data by way of the EDI may encode the data using specific industry notations. In some cases, different healthcare providers (e.g., hospitals, primary care providers, and/or the like) may encode the same data differently. As an example, one healthcare provider may indicate a patient's gender using alphabetic characters "M," "F," and/or the like, while another healthcare provider may indicate a patient's gender using numeric characters "1," "2," and/or the like. Decoding the data communicated by the EDI may prove to be a daunting and difficult task. Some data analytics tools may employ exhaustive computer coding efforts and/or a large number of data processing resources to decode the enormous amount of data communicated by the EDI. In many instances, some data analytics tools include exorbitant licensing fees associated with accessing or obtaining proprietary software to decode the data.

Similarly, the various entities that send, receive, exchange, and/or otherwise communicate data by way of the EDI may encode the data in one of many different EDI formats (e.g., a format according to Health Level Seven (HL7) standards, a format according to National Council for Prescription Drug Programs (NCPDP) standards, a format according to Digital Imaging and Communications in Medicine (DICOM) standards, an extensible markup language (XML) format, a YAML Ain't Markup Language (YAML) format, a JavaScript Object Notation (JSON) format, and/or the like). Some data analytics tools may rely on predefined tables and data structures that transform the data based on a rigid set of rules, typically rules that only transform the data received in a single EDI format. Such rigidity leads to limited data abstraction and restricted analyses. Furthermore, collaboration between different healthcare clients may be inhibited or further complicated, given that the different healthcare clients may utilize different technological infrastructures.

Some implementations described herein provide a flexible, intelligent computing platform, such as a healthcare data platform, for analyzing large amounts of data communicated by a healthcare EDI. In some implementations, the healthcare data platform may be configured to standardize the data communicated by the healthcare EDI, for example, by decoding and/or decoupling the data from specific industry notations and/or EDI formats. In this way, the healthcare data platform may provide a more comprehensive and thorough data analytics platform. The healthcare data platform may utilize standardized data sets and intelligent mappings to perform more efficient, uniform, consistent, and/or automated data transformations using the data communicated by the healthcare EDI. For example, the data received from the healthcare EDI may be converted to a common data format, assigned various attribute identifiers, and/or logically grouped for use in deriving various healthcare metrics. The healthcare metrics may be transmitted or posted to the EDI for consumption by various clients. The clients may additionally be caused to perform one or more actions based on the metrics. As an example, a client may perform actions including paying a claim, denying a claim, enrolling an individual in an insurance policy or plan, assigning a member to a healthcare provider, and/or the like, based on the metrics derived by the healthcare data platform.

In some implementations, a plurality of functions or logic may be stored in one or more collections or libraries available to the healthcare data platform. Such functions may facilitate the provision of common data transformations and/or metric computations using the common data transformations. For example, the logic for computing a common data transformation (e.g., primary care physician attribution, provider matching, KPIs, and/or the like) may be reused, rendering the computation of such functions and metrics more efficient, automated, and/or consistent. In this way, coding efforts and computing resources that would otherwise be needed to perform multiple iterations of the common data transformation of data are greatly reduced or obviated.

Additionally, or alternatively, the healthcare data platform may use machine learning and/or artificial intelligence to make intelligent predictions, mappings, and/or groupings of data to improve the overall process of performing data transformations and analyses. For example, the healthcare data platform may train data models on historical data that may be used to predict and/or classify newly obtained data from the healthcare EDI, by assigning the data to specific healthcare subject areas, deriving lists of possible metrics based on data elements present in the newly obtained data, and/or the like. In this way, the analysis of data obtained from the healthcare EDI may be more automated, efficient, and consistent. Further, the amount of computing resources needed to decode the data received from the healthcare EDI may be obviated or reduced.

The healthcare data platform may improve an efficiency of analyzing healthcare data associated with processes and/or operations being performed by various data sources or clients. In addition, the intelligent predictions and/or mappings employed by the healthcare data platform may conserve processing resources that would otherwise be consumed by efforts to decode the data obtained from the EDI, perform rigid transformations of the data, and/or perform inefficient operations.

In some cases, a data analyst, a data scientist, a business analyst, and/or another user may seek certain analytical information relating to data (e.g., healthcare data) and/or data elements (e.g., metadata) relating to the data stored in a computing platform (e.g., a healthcare data platform). For example, a user may want to learn about how a particular metric was derived, identify a source of particular data and/or a metric, determine a rule by which a particular data element was cleansed, transformed, computed, and/or aggregated, and/or other analytical information. However, as data sets and/or data sources continue to grow in volume, velocity, and variety, more traditional "single versions of truth" of data sets shift to "distributed truth sets," making it difficult for a user to trace analytical information about particular data. A user may need to spend significant amounts of time and resources to manually sort through the data sets, the data sources, and/or associated applications in order to obtain such analytical information.

Some implementations described herein provide a digital assistant platform that may operate in conjunction with the healthcare data platform to help identify, determine, and/or provide such analytical information. Analytical information may correspond to a data attribute, a data definition, a data location, a data derivation, a data lineage, a data cleansing rule, a data transformation rule, a data computation rule, a data aggregation rule, and/or other information associated with the data that may not otherwise be available to a user accessing the healthcare data platform. For example, the digital assistant platform may provide a plurality of pre-defined services that may be stored in one or more collections or libraries and configured to determine different types of analytical information about data elements of the healthcare data platform. The digital assistant platform may be configured to selectively call and/or enable one or more of the services to determine a particular type of analytical information associated with a particular data element of the healthcare data platform.

In some implementations, the digital assistant platform may provide a user interface (e.g., a chatbot and/or the like) that enables a user to access data managed by the healthcare data platform and/or analytical information associated with the data. For example, the user interface may enable a user to submit a query (e.g., in a natural language format) relating to a data file of interest (e.g., a target data file) that is managed by the healthcare data platform. The digital assistant platform may receive the query, extract one or more keywords from the query, and use the keywords to identify an intent classification and/or an entity associated with the query. The digital assistant platform may extract the keywords from the query using a natural language processing model, and identify the intent classification and/or the entity using a machine learning model. The digital assistant platform may identify one or more of the services to enable based on the intent classification, identify the target data file based on the entity, and use the services and the target data file to determine analytical information associated with the target data file. The digital assistant platform may generate a response to the query based on the analytical information (e.g., via the chatbot and/or another user interface), and/or cause another action to be performed based on the analytical information.

In this way, the digital assistant platform may facilitate a process by which a user obtains analytical information relating to data elements of large data sets. For instance, by providing a chatbot interface that leverages a natural language processing model, the digital assistant platform allows users with varying levels of skill to submit a simple query and learn more information about data with minimal effort. Furthermore, by using a machine learning model to interpret the query, retrieve the analytical information sought by the user, and prompt the user for more information if needed, the digital assistant platform is able to provide the user with more relevant results in fewer interactions. In addition, the machine learning model of the digital assistant platform may use interactions with the user and patterns in the interactions as learning points to provide more accurate results over time. Also, by providing access to a library of diverse services capable of analyzing data elements of a data set in a number of different ways, the digital assistant platform offers the user a wide range of analytical information. The digital assistant platform thereby conserves significant amounts of time, manual effort, computational resources, and/or network resources that may otherwise be used to determine analytical information associated with a data element.

While some implementations described herein are described in the context of healthcare data, one or more of these implementations may be applied outside of the healthcare data context. For example, one or more of these implementations may be applied in other contexts, such as in a financial data context, a government record context, a military record context, a census data context, and/or the like.

FIGS. 1A-1E are diagrams of an example implementation 100 described herein. As shown in FIGS. 1A-1E, example implementation 100 may include a healthcare data platform. The healthcare data platform may include standardization engine(s), which may include transformation algorithm(s), data transformation algorithm(s), and reusable methods and functions for carrying out data transformations on healthcare data sets (e.g., deriving member spans from multiple coverages, member matching, provider matching, healthcare claims submissions to Centers for Medicare & Medicaid Services (CMS), and/or the like). The healthcare data platform may further include metric derivation engine(s), which may generate various metrics. The healthcare data platform may further include mapping engine(s), which may include subject area mappings, KPI library mappings, and/or attribute mappings. The healthcare data platform may generate a standardized data set and, in some implementations, employ intelligent mappings for mapping data elements in the standardized data set to functions in a common function library, functions in a KPI library, and/or a subject area repository.

As shown in FIG. 1A, and by reference number 102, a plurality of data source devices may send a plurality of data files. The data source devices may include computers or servers associated with one or more healthcare entities (e.g., healthcare providers, offices, hospitals, pharmacies, insurance companies, and/or the like). In some implementations, the data source devices may transmit the data files using a healthcare EDI. The data files may include or contain healthcare data or healthcare related data, including, for example, health insurance data, health insurance claims data, patient or member data, enrollment data, medical records, pharmaceutical records, payment records, billing records, and/or the like. In some implementations, the healthcare data may be encoded as data elements (e.g., metadata) in the data files. The healthcare data platform can receive and analyze millions, billions, trillions, and/or another quantity of data records and/or data elements, the volume of which cannot be processed objectively by human actors.

In some implementations, the data elements contained in the data files may indicate information relating to a patient (e.g., a patient gender, name, member identifier, age, date of birth, and/or the like), information relating to a medical claim (e.g., date(s) of service, a healthcare provider identifier, a billed amount, a paid amount, a denied amount, and/or the like), information relating to a medical condition or treatment (e.g., medical condition(s) identified, medical service(s) performed or received, lab work performed, pharmaceuticals prescribed, and/or the like), information relating to a healthcare provider (e.g., a hospital identifier, a physician or doctor identifier, and/or the like), and/or the like.

In some implementations, the plurality of data files sent by the plurality of data source devices may be transmitted in a plurality of different data formats. Example data formats include, without limitation, HL7 messaging formats, NCPDP messaging formats, DICOM messaging formats, XML, messaging formats, JSON messaging formats, and/or the like.

As further shown in FIG. 1A, and by reference number 104, the healthcare data platform may receive the data files from the plurality of data source devices. In some implementations, the healthcare data platform may receive the data files from the healthcare EDI. For example, the healthcare data platform may subscribe to receive data from the healthcare EDI. In some implementations, the data files may be received in one or more different ways. For example, the data files may be streamed, obtained using application programming interface (API) calls, pushed, fetched, and/or received in batches from the healthcare EDI.

As indicated above, the data files may be sent by the data source devices and received by the healthcare data platform in multiple different data formats. In some implementations, the healthcare data platform may convert the data files received in the multiple different data formats to a common data format. As an example, the data files received in HL7, DICOM, XML, JSON, and/or NCPDP messaging formats may be converted to Comma Separated Value (CSV) files using code or logic to perform the CSV conversion. Example files are shown in FIG. 1A.

Continuing with respect to reference number 104, as shown, the healthcare data platform may convert a first data file received from a first data source to a first CSV file having the file identifier "File 1," and the healthcare data platform may convert a second data file received from a second data source to a second CSV file having the file identifier "File 2." In some implementations, the healthcare data platform may convert the incoming or received data files to the same CSV format. For example, assume that the data elements in the first data file correspond to a plurality of member identifiers and genders associated with the member identifiers. Here, assume that the first data source transmitting the first data file uses the alphabetic characters "M," "F," and "B" to indicate the member's gender. Further assume that the data elements in the second data file also correspond to a plurality of member identifiers and genders associated with the member identifiers. However, in contrast to the notations employed by the first data source, assume that the second data source uses numerals "1," "2," and "3" to indicate the member's gender. As described herein, the healthcare data platform may apply a data standardization reference rules library to determine that "M" and "1" both identify the same attribute (e.g., male).

In some implementations, the healthcare data platform may validate the decimal and integer fields associated with the data elements in the data files during or after conversion to the common data format. For example, for data elements associated with a date, the healthcare data platform may convert multiple date formats (e.g., 01/01/2018, 01-01-2018, 01/11/18, and/or the like) to a common data format. In some implementations, the decimal and integer fields may be validated to ensure that the data elements are consistent with the common data format.

Figure 1B:
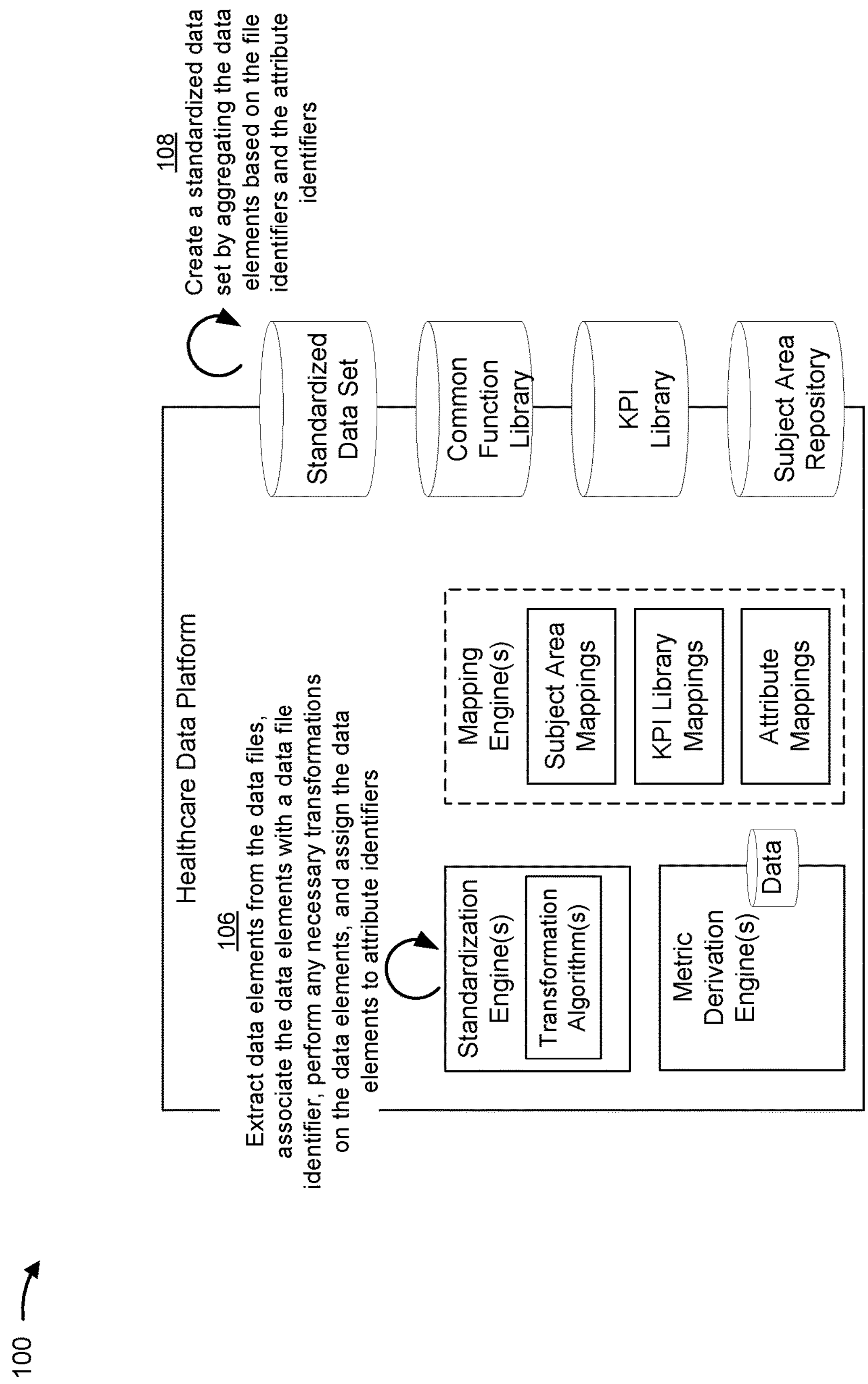

As shown in FIG. 1B, and by reference number 106, the healthcare data platform may extract the data elements from the data files converted to the common data format, associate the data elements with file identifiers (e.g., "File 1," "File 2," and/or the like), perform any necessary transformations on the data elements, and assign the data elements to attribute identifiers. The attribute identifiers may be predetermined, standardized, and/or predefined identifiers that label, classify, or otherwise identify the type of data (e.g., member data (e.g., health insurance member identifier, age, date of birth, and/or the like), claim data (e.g., service date, claim amount, balance due, and/or the like), healthcare provider data (e.g., healthcare provider identifier, hospital identifier, healthcare provider address, and/or the like), pharmacy data (e.g., a prescription identifier, a medication identifier, and/or the like), and/or the like) that is represented by the respective data element. In this way, the data received from the healthcare EDI may be standardized and homogenized, for example, using one or more standardization engines of the healthcare data platform.

Initially, in some implementations, the healthcare data platform may extract the data elements from the data files and associate the extracted data elements with file identifiers. In this case, the file identifiers may identify a data file from which the data elements are extracted. For example, the member identifier and gender data elements may be extracted from the first CSV file, as described above with respect to FIG. 1A, and may be associated with the file identifier "File 1." Similarly, the member identifier and gender data elements may be extracted from the second CSV file, as described above with respect to FIG. 1A, and may be associated with the file identifier "File 2." The healthcare data platform may perform the data file conversion, data element extraction, and data element assignment for thousands, millions, billions, and/or the like, of data files over any given time period (e.g., an hour, a day, a week, and/or the like).

In some implementations, the healthcare data platform may perform preliminary cleansing of the data elements before assigning the data elements to attribute identifiers to ensure elimination of redundant data and ensure that valid data is processed by the healthcare data platform. The invalid data may be reconciled by error handling routines. In this way, the healthcare data platform may perform common data validation of data elements in a data set to eliminate redundancy without compromising validity. For example, the transformation algorithms and/or functions obtained from the common function library may be used to deduplicate redundant data elements in the data files and/or match claims to adjudicated amounts for use in determining various metrics as described further below.

In some implementations, the healthcare data platform may assign, label, or classify the extracted data elements in the data files based on predetermined or predefined attribute identifiers. In this way, any specific notations (e.g., "M," "F," "1," "2," and/or the like) may be removed, obviated, standardized, and/or homogenized. In some implementations, the healthcare data platform may access data structures or mappings for assigning the data elements to the attribute identifiers. For example, the healthcare data platform may employ one or more mapping engines based on a healthcare subject area and one or more attribute data structures containing mappings (e.g., tables, catalogs, databases, and/or the like) to assign or map the data elements and the predefined attribute identifiers. Continuing with the example in FIG. 1A, the "M" in File 1 and the "1" in File 2 may each be assigned to the attribute identifier "Male." In this way, the data files are assigned to standardized attribute identifiers. Similarly, the "F" in File 1 and the "2" in File 2 may each be assigned to the common attribute identifier "Female." Similarly, the "B" in File 1 and the "3" in File 2 may each be assigned to the common attribute identifier "Non-Identifying." In this way, occurrences of different notations may be obviated from a data set, which conserves computing resources that would otherwise be needed to decode the data elements upon using the data elements to calculate metrics or KPIs.

In some implementations, the data structures or mappings used to assign the data elements to the attribute identifiers may be compiled based on historical data and a machine learning model. For example, the machine learning model may use, as input, historical data based on knowledge of the data element notations being implemented by specific data sources to determine assignments for newly received data elements in data files received from the same data sources. For example, the healthcare data platform may receive a file from the first data source, which the healthcare data platform recognizes as Hospital Z. The healthcare data platform may determine, based on examining historical data input to a client mapping rules engine, that Hospital Z encodes gender in the form of "1" for males, "2" for females, and "3" for non-identifying individuals. Based on this historical data, the healthcare data platform may determine that File 2 is from Hospital Z and automatically assign the data element "1" to the attribute identifier "Male" when assigning the data elements to attribute identifiers for File 2. In this way, for example, and based on this assignment scheme, computing resources that would otherwise be needed to assign the data elements to attribute identifiers may be conserved.

In some implementations, the healthcare data platform may be configured to assign the data elements to attribute identifiers based on a data model that classifies the data file according to a pattern or combination of data elements present in the data file. For example, the healthcare data platform may perform a high-level scan or assessment of a data file, upon re-formatting the data file, to initially determine what kind of information may be present in the data file. As a specific example, the healthcare data platform may scan File 2 and determine, based on the presence of the member identifiers and gender information, that File 2 is a data file for membership enrollment. Assuming that additional data elements were present in File 2, the healthcare data platform may determine which attribute identifiers to assign to the additional data elements based on determining which additional data elements, if any, are commonly present in data files for membership enrollment. For example, File 2 may include unidentified numeric values (e.g., ranging between 0-100) associated with each member identifier and gender, and the healthcare data platform may determine, using the data model, to assign the unidentified numeric values to the attribute identifier "Age" based on knowledge and/or prediction that membership enrollment files typically include member identifiers, gender, and ages.

Accordingly, in some implementations, the healthcare data platform may examine a data file, of the plurality of data files, to identify a pattern or combination of data elements present in the data file. The healthcare data platform may determine, using a machine learning model, a score (e.g., a map score) for a data element in the data file based on the combination of data elements present in the data file. The score may predict a type of healthcare data (e.g., the member's age, in the example above) represented by the data element based on the combination of data elements present in the data file. The healthcare data platform may then assign the data element to an attribute identifier based on the score. The data files may be classified as containing or identifying data pertaining to claim types, claim status, member types, product codes, facility types, insurance network types, adjudication outcomes, and/or the like. Data elements within such data files may be intelligently assigned to attribute identifiers based on the type of data the model predicts will be present within a given type of data file.

As further shown in FIG. 1B, and by reference number 108, the healthcare data platform may create or form a standardized data set by aggregating the data elements based on the data file identifiers and the predetermined attribute identifiers. The standardized data set may be devoid of industry or data source specific notations and/or specific EDI formats. In some implementations, the data associated with the attribute identifiers contained in the standardized data set may have been transformed using a function or logic, such as by using, for example, a common transformation algorithm or a common function.

In this way, computing resources associated with extracting, transforming, and/or aggregating data based on different logic (e.g., different algorithms, differently coded functions, and/or the like) for data elements specified in differing formats are reduced or obviated. The standardized data set may be used to derive, determine, compute, or calculate various healthcare metrics and/or KPIs. Various actions may be performed based on determining the healthcare metrics and/or KPIs as described below.

In some implementations, data clients, including healthcare data clients, may subscribe or otherwise access the standardized data set stored by the healthcare data platform to perform various data analyses. In this way, utilizing the standardized data set may improve the efficiency at which the various data analyses are performed. In some implementations, the healthcare data platform may calculate metrics that are accessed, used, and/or consumed by multiple data clients. In this way, the metrics may be consistently calculated irrespective of specific notations and/or EDI formats. Computing resources that would otherwise be needed to calculate the metrics for individual data clients based on specific notations and/or EDI formats are conserved, reduced, and/or obviated.

Figure 1C:
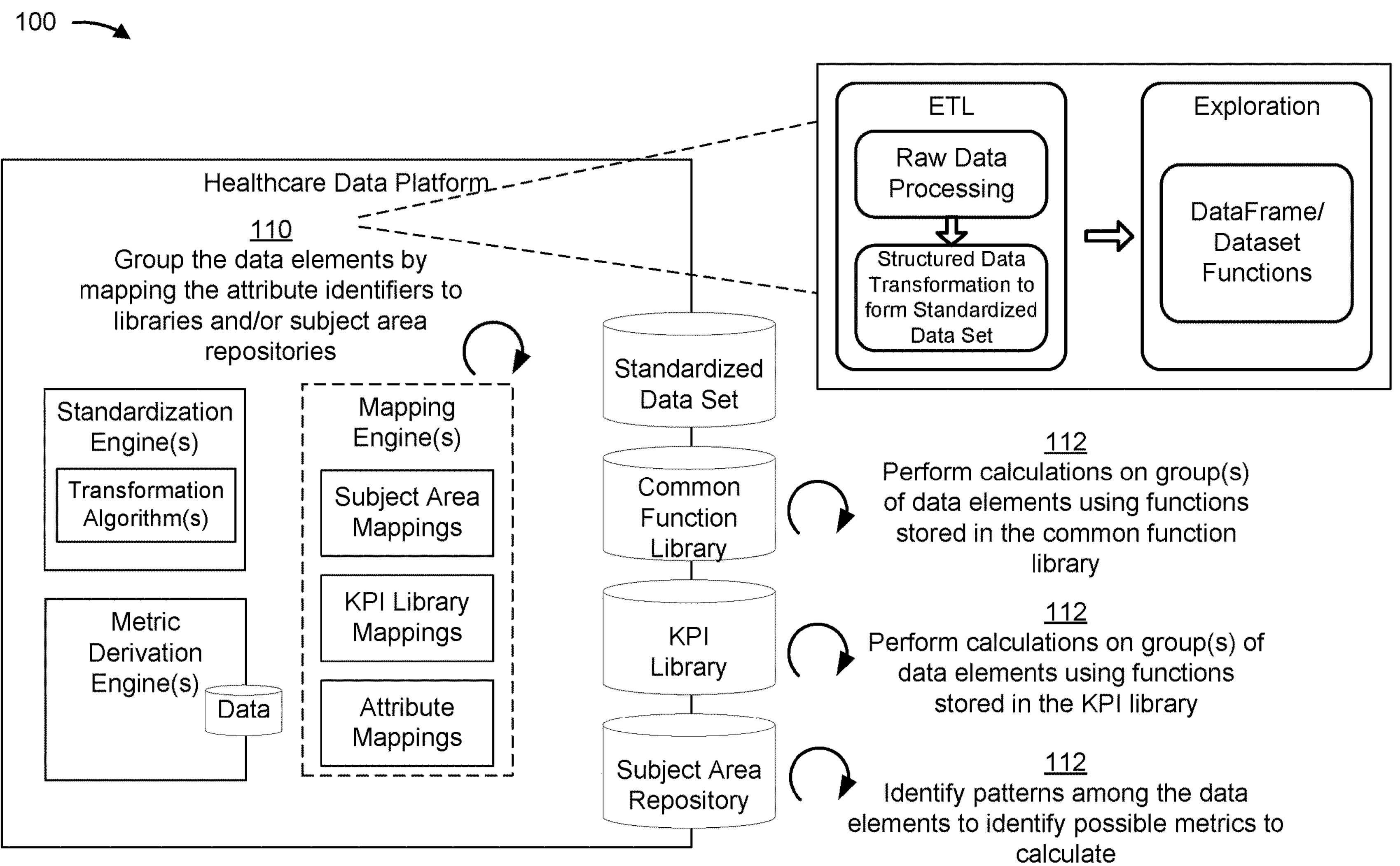

As shown in FIG. 1C, and by reference number 110, the healthcare data platform may group the data elements in the standardized data set. In some implementations, the data elements in the standardized data set may be grouped based on mapping the predetermined attribute identifiers associated with the data elements to libraries and/or subject area repositories for which the data elements may be used to perform various analyses. In some implementations, the healthcare data platform may access one or more mapping engines to map the data elements in the standardized data set to a plurality of functions contained in at least one function library, such as the common function library or the KPI library, based on a mapping between the attribute identifiers and the plurality of functions. In some implementations, the healthcare data platform may map the data elements in the standardized data set to one or more subject area repositories based on mappings between the attribute identifiers and the subject area repositories. In this way, the data sets undergo intelligent processing based on the types of data elements and automate KPI calculation depending on the subject area of the client providing extended insights to the clients.

Continuing with respect to reference number 110, as the inset in FIG. 1C shows, the raw data may be extracted, transformed, and/or loaded (i.e., ETL) into a data structure containing the standardized data set (e.g., using structured data transformations). The data in the standardized data set may be mapped to functions or repositories for further exploration and insight using the data. In some implementations, the data elements in the standardized data set may be grouped into data frames and mapped to the subject area repository, the common function library, the KPI library, and/or the like. The groupings may be based on subject area mappings, common function library mappings, and/or KPI library mappings accessed by the one or more mapping engines.

In some implementations, the healthcare data platform may intelligently group the data elements based on machine learning models or data models by which the healthcare data platform predicts the subject area repository, the common function, and/or the KPI to which the data elements correspond. For example, the healthcare data platform may examine a data file to identify a combination of data elements present in the data file. The healthcare data platform may determine, using a machine learning model or a data model, a score for the data file based on the combination of data elements present in the data file. The score may predict a subject area (e.g., a healthcare subject area) associated with the data file based on the combination of data elements present in the data file. The healthcare data platform may assign the data file and/or data elements in the data file to a subject area repository based on the score.

In this way, standardized data sets for various subject areas may be created for use in calculating various metrics specific to a given subject area. Example subject areas include, for example, a Pharmacy Claim subject area, a Provider subject area, a Medical Claim subject area, a Member subject area, and/or the like. Data files and/or data elements used to perform specific subject area operations may be assigned to and/or stored in the various subject area repositories. As an example, a primary care provider (PCP) repository may include data files and/or data elements used to perform PCP-specific operations including PCP attribution, PCP matching, and/or the like. A health insurance claims subject area repository may include data files and/or data elements used to perform claims-specific operations or calculations, including, for example, calculations for determining late payment penalties incurred on adjusted claims, the number of claims denied during a specified period, the average claim processing or cycle time, the total number of claims received, and/or the like.

In some implementations, the data elements may be assigned to subject area repositories and/or functions based on unique keywords specific to the subject area and/or function. For example, incoming data files including the keywords "dependent" and/or "qualified health plan (QHP)" may be correlated and/or assigned to a member subject area repository and/or functions that may utilize member information contained in such data files. Similarly, data files that include keywords related to a specific payer or a specific diagnostic code may be correlated and/or assigned to a health insurance claims subject area repository and/or functions that may utilize claims information contained in such data files.

In some implementations, the healthcare data platform may intelligently map data elements in the standardized data set and/or the subject area repositories to KPIs contained in the KPI library. Various KPIs may be defined or configured in the KPI library. The KPI definitions or configurations may include mathematical formulas based on manipulating data elements that correspond to specified attribute identifiers. In some implementations, the attribute identifiers in the standardized data set and/or subject area repositories may be identified, matched to KPI definitions, and mapped to the KPI definitions in the KPI library.

As further shown in FIG. 1C, and by reference number 112, the healthcare data platform may perform various actions based on the groupings or mappings between the attribute identifiers, the libraries (e.g., common function library, KPI library, and/or the like), and/or the subject area repositories. For example, the healthcare data platform may perform calculations based on the data elements mapped to functions stored in the common function library. Example common functions include calculating amounts for paid claims, calculating amounts for denied claims, or calculations based on the life cycle of a claim. Additionally, or alternatively, the healthcare data platform may perform calculations based on the data elements mapped to functions stored in the KPI library. Example KPIs include average claim processing times, patient wait times, average lengths of stay, claim denial rates, average treatment charges by a provider, and/or the like.

Additionally, or alternatively, the healthcare data platform may identify patterns (e.g., utilizing a data model, a machine learning model, or other intelligence) among the data elements in the standardized data set and/or the subject area repositories to identify possible metrics that may be calculated based on the data elements present in the standardized data set and/or the subject area repositories. For example, the healthcare data platform may examine the standardized data set or subject area repository to identify the attribute identifiers present in the standardized data set or the subject area repository, may determine, using a data model, a list of healthcare metrics that are derivable from the standardized data set or the subject area repository based on the attribute identifiers present in the standardized data set or the subject area repository, and may present the list healthcare metrics that are derivable from the standardized data set or the subject area repository to one or more healthcare data clients.

In some implementations, the data model used to determine the metrics in the list of healthcare metrics that may be derivable from the standardized data set may be trained on training data that includes patterns of attribute identifiers. The healthcare data platform may identify a metric to include in the list of metrics using pattern recognition based on recognizing the patterns in the attribute identifiers, and generate a score (e.g., a KPI score) that predicts the ability to successfully determine the metric. The score may be compared to a threshold value (e.g., a confidence level), by which the healthcare data platform will include the metric in the list of metrics if the threshold is satisfied.

Figure 1D:
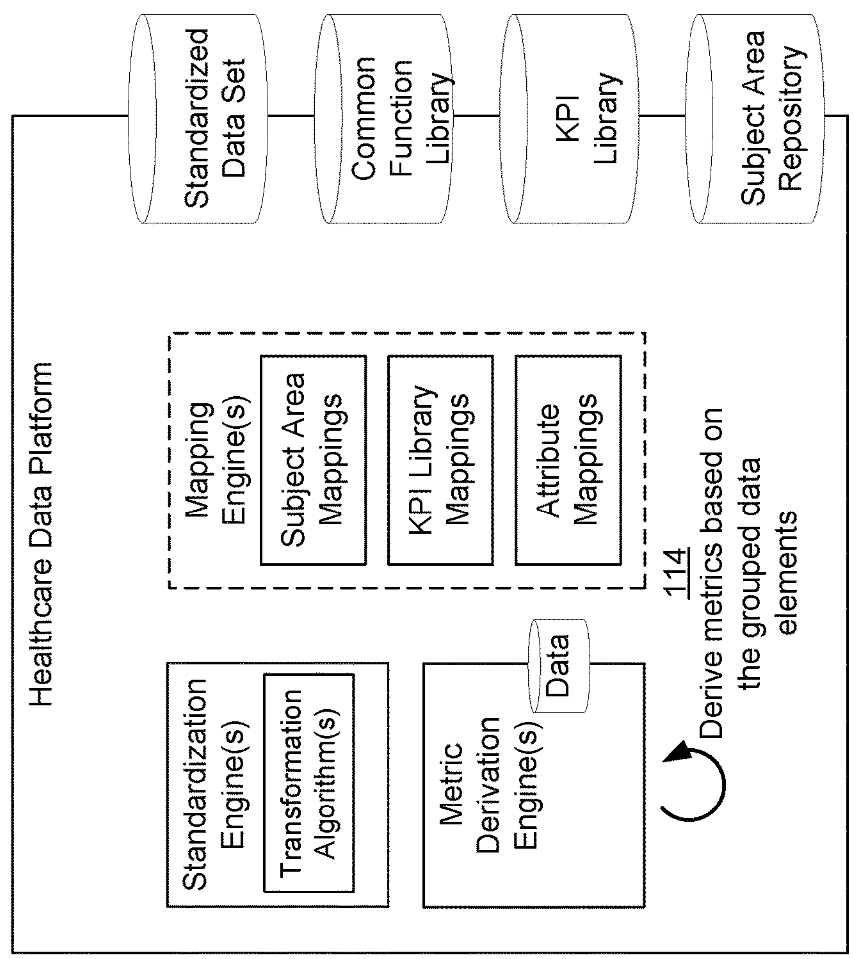

As shown in FIG. 1D, and by reference number 114, the healthcare data platform may derive, determine, generate, calculate, or compute metrics (e.g., healthcare metrics) based on the grouped data elements. For example, in some implementations, the healthcare data platform may generate a plurality of values based on mapping the data elements to the plurality of functions and may determine one or more metrics based on combining the plurality of values according to a metric definition or logic. In some implementations, the metrics may be determined by a metric derivation engine of the healthcare data platform, which accesses stored metric definitions and computes the metrics based on the stored definitions. Example metrics include per member per month (PMPM) metrics, member satisfaction metrics, community metrics (e.g., metrics relating to childhood immunizations, births, deaths, diseases, and/or the like), hospital metrics (e.g., average length of stay in a hospital, readmission rates, wait times, and/or the like) and/or the like.

Figure 1E:
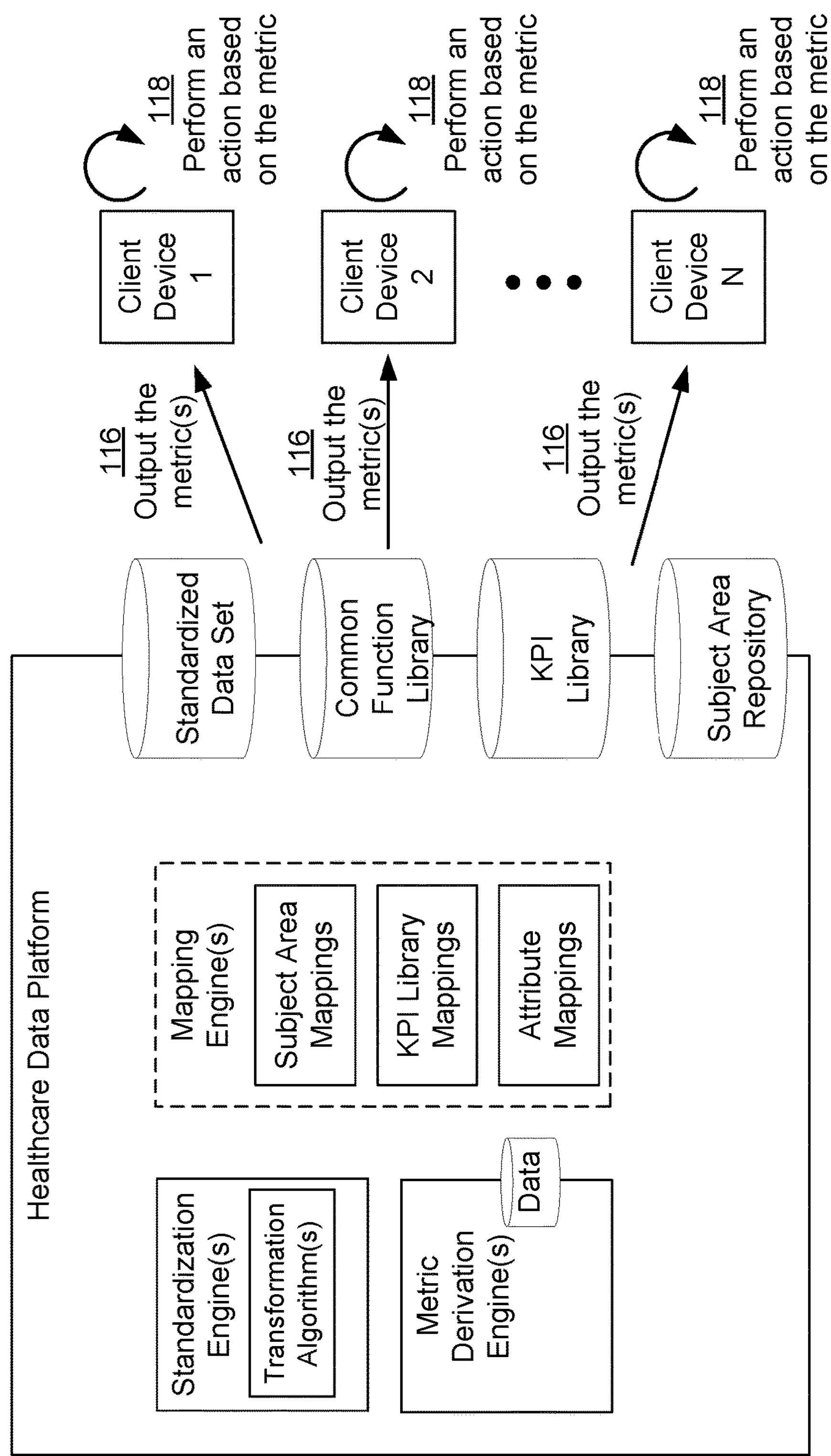

As shown in FIG. 1E, and by reference number 116, the healthcare data platform may output the generated metrics. The healthcare data platform may post the metrics to the healthcare EDI for consumption by one or more client devices (e.g., healthcare data client devices), export the metrics to the one or more client devices, stream the metrics to the one or more client devices, post the metrics to a client file system, and/or the like.

As shown by reference number 118, one or more actions may be performed based on determining the metrics. As examples of such actions, a client device may be caused to pay a claim, deny a claim, enroll an individual in an insurance policy or plan, assign a member to a healthcare provider, and/or the like, based on the metrics output by the healthcare data platform. Further, a machine (e.g., a computer, a mobile device, and/or the like) may be used to take a healthcare measurement, check a member into a healthcare facility or institution (e.g., using a self-check-in kiosk, a mobile device, and/or the like), cause a device in a healthcare facility or institution to power on or power off, cause a notification to be provided to a healthcare provider, a claims provider, and/or an individual, and/or the like. Further examples of actions that may be performed based on determining the metrics include causing a payment to be made, adding benefits or services provided to a patient, automating communications between healthcare entities, reducing waiting times in a healthcare facility or institution, scaling up computing resources for processing payments or claims by a healthcare entity, and/or the like. In this way, automated metric determination and/or output improves the efficiency and timeliness of performing actions based on the metrics.

In this way, a healthcare data platform may be provided that is flexible, scalable, and incorporates intelligent groupings or mappings to create one or more standardizing data sets based on data files having different notations and/or EDI formats. By standardizing and intelligently mapping the millions, billions, or more data files or records received from the healthcare EDI, computing resources that would otherwise be needed to decode individual data files are conserved, reduced, and/or obviated. Furthermore, the healthcare data platform may automate the generation or derivation of metrics from standardized data sets and, thus, conserve resources that would otherwise be needed to manually generate such metrics.

In this way, several different stages of the process for data extraction, transformation, and loading are automated, which may remove human subjectivity and waste from the process, and which may improve speed and efficiency of the process and conserve computing resources (e.g., processor resources, memory resources, and/or the like). Furthermore, implementations described herein use a rigorous, computerized process to perform tasks or roles that were not previously performed or were previously performed using subjective human intuition or input. For example, currently there does not exist a technique to automate data extraction, transformation, and loading for data files having different notations and/or formats. Finally, automating the process for data extraction, transformation, and loading as described herein conserves computing resources (e.g., processor resources, memory resources, and/or the like) that would otherwise be wasted in attempting to decode data files, identify attributes, and/or generate metrics.

As indicated above, FIGS. 1A-1E are provided merely as an example. Other examples are may differ from what is described with regard to FIGS. 1A-1E.

Figure 2A:
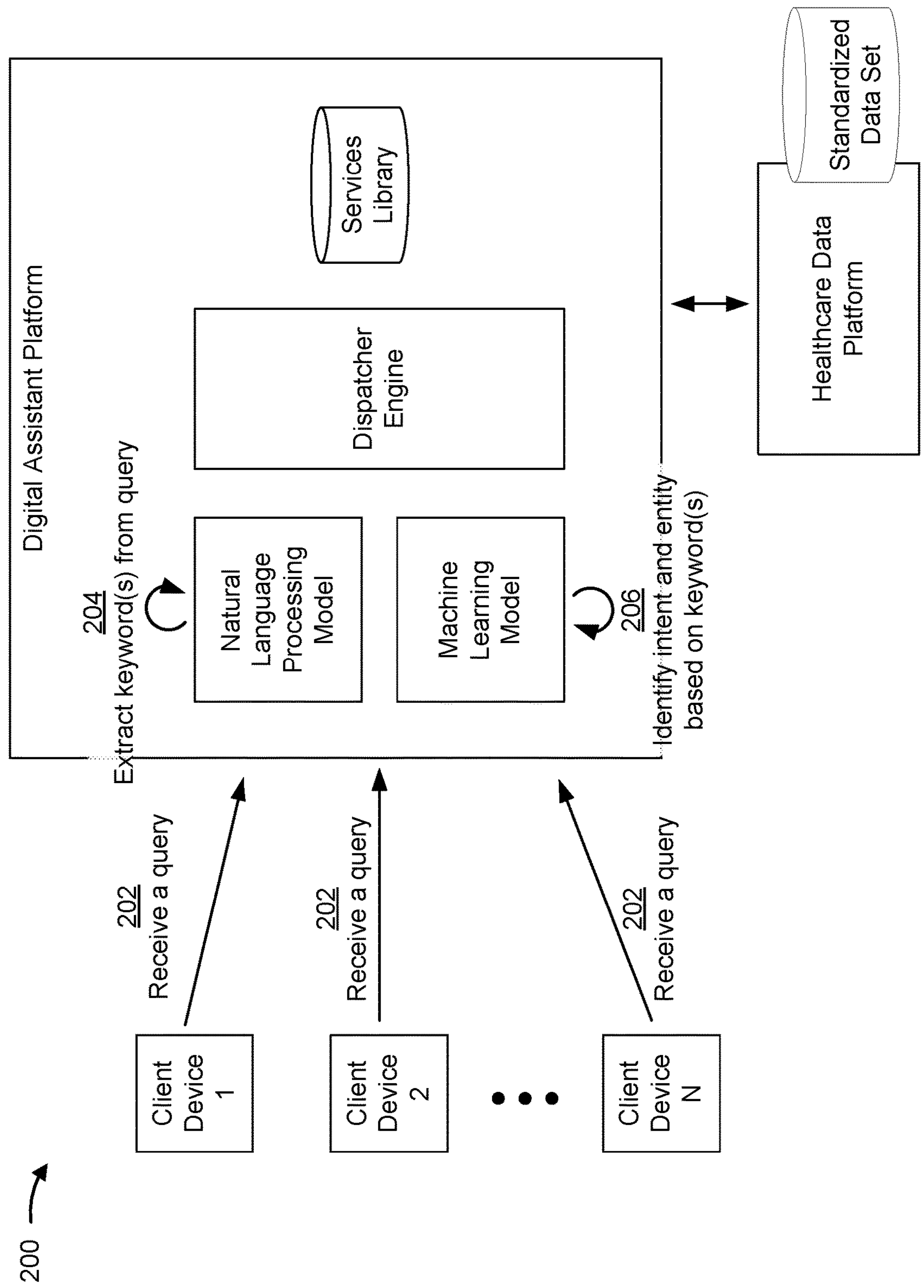
FIGS. 2A-2C are diagrams of another example implementation described herein.
Figure 2B:
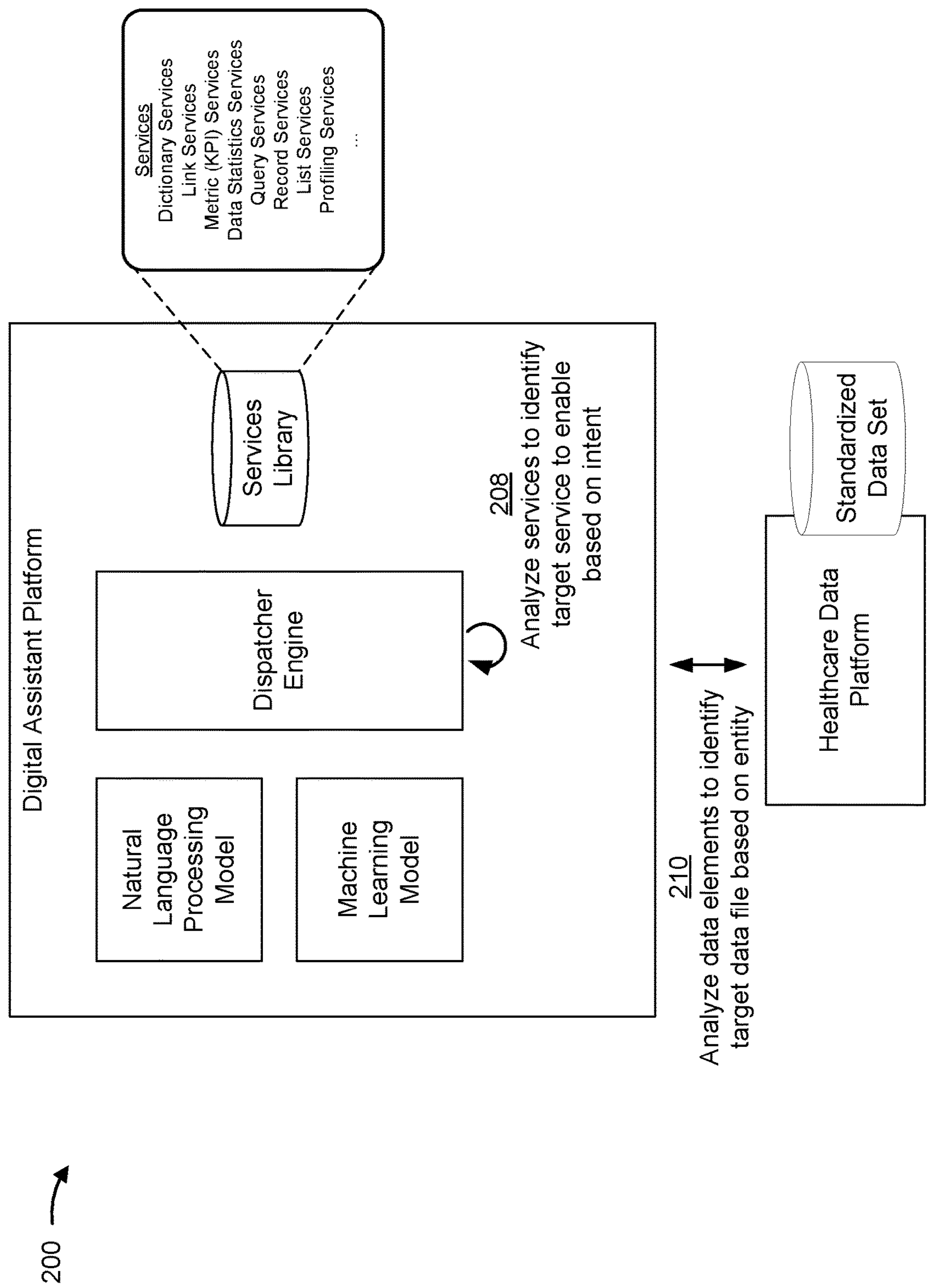
Figure 2C:
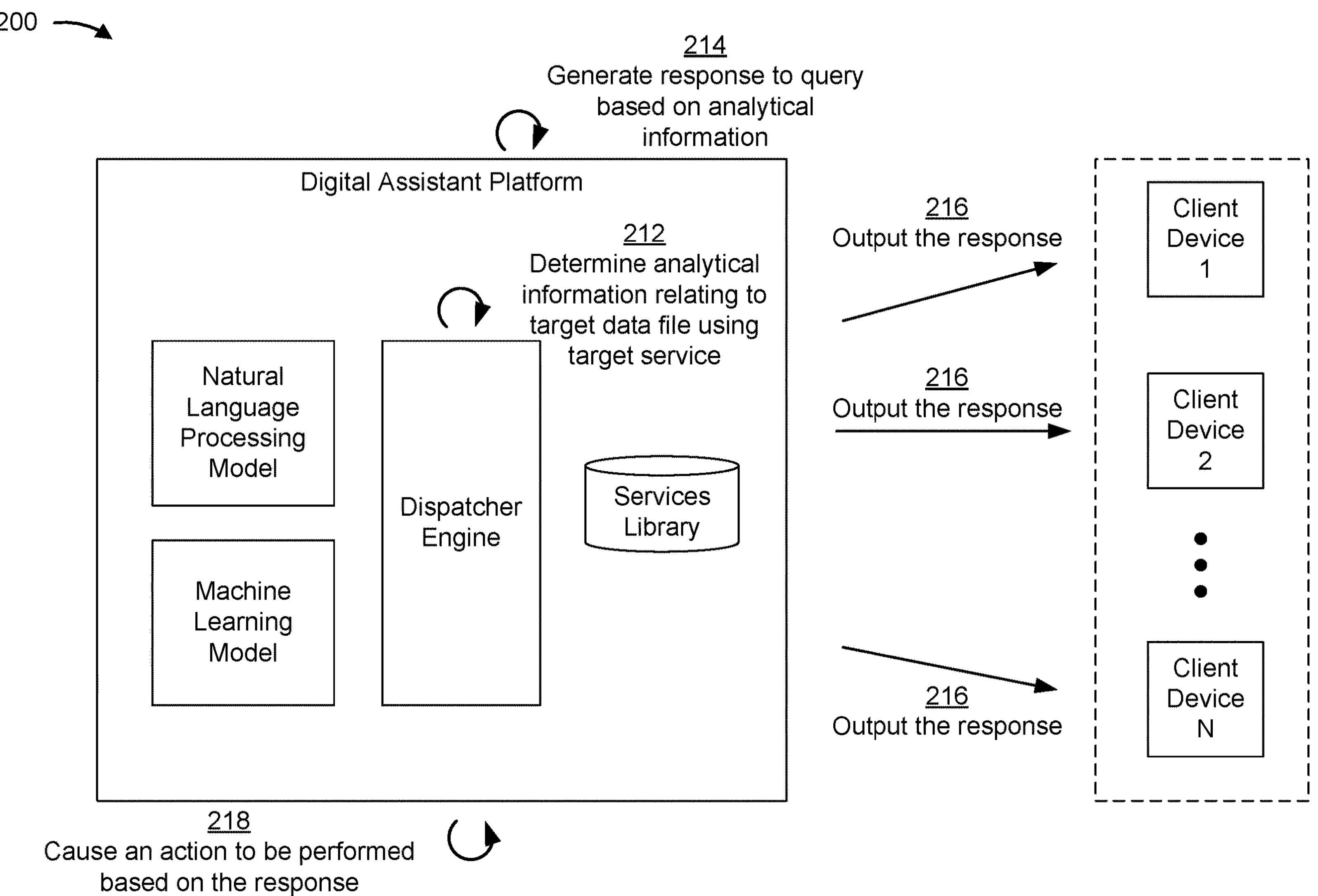

FIGS. 2A-2C are diagrams of an example implementation 200 described herein. As shown in FIGS. 2A-2C, example implementation 200 may include a digital assistant platform that may be used in conjunction with a healthcare data platform. For example, the digital assistant platform may be provided separately from, but in communication with, the healthcare data platform. In some examples, the digital assistant platform may be at least partially implemented within the healthcare data platform. As shown, the digital assistant platform may include a natural language model, a machine learning model, a dispatcher, and a services library that collectively provide a user interface to the healthcare data platform and enable one or more client devices to access analytical information associated with data managed by the healthcare data platform. FIGS. 2A-2C present one or more functions that may be performed by the digital assistant platform to identify, determine, and/or provide the analytical information to a user via a user interface. In some examples, one or more of the functions, described herein as being performed by the digital assistant platform, may be performed by the healthcare data platform, the client device, and/or another device (e.g., the data source device).

In some implementations, the digital assistant platform may be used in association with a digital assistant service that is supported by the digital assistant platform, the healthcare data platform, and/or the client device. For example, the digital assistant service may be used by a user (e.g., a healthcare data client, another type of data client, a data analyst, a data scientist, a business analyst, and/or another subscriber) to access data files, data elements, and/or analytical information based on a standardized data set managed by the healthcare data platform, as described above. The digital assistant service may provide a user interface that enables a user to select a topic of interest, navigate through categories or aggregations of data within the standardized data set, perform data analyses using data elements of the data, and/or submit a query relating to analytical information associated with the data elements. In some examples, the user interface may be provided in a form of a chatbot interface that is configured to interact with the user using a natural language format and retrieve information sought by the user. A user may access the digital assistant service using the client device (e.g., a computer, a smart phone, a mobile device, and/or the like) over a wired connection and/or a wireless connection to the digital assistant platform.

As shown in FIG. 2A, and by reference number 202, the digital assistant platform may receive a query relating to a target data file. For example, the digital assistant platform may receive the query from a user (e.g., via a client device with access to a digital assistant service). The target data file may be associated with a standardized data set managed by the healthcare data platform and/or another computing platform. As described above, the standardized data set may include a plurality of data files that are aggregated based on respective data elements (e.g., based on data file identifiers, attribute identifiers, and/or the like). In some examples, the standardized data set may be configured to enable a plurality of services (e.g., services provided via the services library of the digital assistant platform) to be used with the plurality of data elements. The digital assistant platform may provide a chatbot interface configured to receive the query from the user as textual data and/or audio data corresponding to a string of characters arranged in a natural language format. In some examples, the digital assistant platform may be configured to receive a plurality of queries from the user, prompt the user with a request for additional information, and/or the like to refine the query.

In some implementations, the digital assistant platform may prompt the user to select a topic from a plurality of topics to refine the query. For example, the digital assistant platform may provide the user with a plurality of topics that are mapped to corresponding aggregations of data files and/or data elements of the standardized data set. In some examples, the topics may relate to an infrastructure of the associated computing platform (e.g., the healthcare data platform), a library function, an inbound data format, a data source format, a data quality metric, a client report, a device support function, a data domain function, a machine learning function, an artificial intelligence function, a business intelligence function, an accelerator function, an aggregation function, a visualization function, and/or the like. The digital assistant platform may provide the user with the available topics associated with the standardized data set, and enable the user to select one or more of the topics that are relevant to the query. The digital assistant platform may prompt the user to select a topic before receiving the query, after receiving the query, in conjunction with the query, and/or in lieu of the query. A topic selected by the user may be used to limit a scope of the functions and/or analyses performed by the digital assistant platform to the aggregation of data files and/or data elements that correspond to the selected topic.

In some implementations, the digital assistant platform may receive a user identifier associated with the query. The user identifier may enable the digital assistant platform to identify the user submitting the query and/or otherwise associate the query with the user. In some examples, the digital assistant platform may receive the user identifier directly from the user (e.g., via the chatbot interface) before receiving the query, after receiving the query, and/or in conjunction with the query. In some examples, such as when the user is subscribed to the digital assistant service supported by the digital assistant platform, the user identifier may be obtained based on registration information supplied by the user upon subscribing to the digital assistant service. The user identifier may include information identifying a general role of the user (e.g., a healthcare provider, an insurance client, and/or the like), and/or a specific role of the user within an organization (e.g., a role within an enterprise associated with the healthcare data platform, and/or the like). In some examples, the digital assistant platform may be configured to authenticate the user based on the user identifier, determine an access level for the user based on the role of the user, and/or filter information that is provided to the user based on the access level to ensure that confidential and/or sensitive information is not shared with an unauthorized user.

As further shown in FIG. 2A, and by reference number 204, the digital assistant platform may extract one or more keywords from the query. For example, if the query corresponds to a string of characters arranged in a natural language format, the digital assistant platform may use a natural language processing model to extract the keywords (e.g., words that are related to data files and/or data elements of the standardized data set) from the query. The natural language processing model may be trained to extract the keywords from a string of characters corresponding to the query by tokenizing (e.g., extracting words from the string of characters corresponding to the query), filtering (e.g., removing unrelated words from the query), stemming (e.g., reducing inflected words to a base form), lemmatizing (e.g., grouping inflected forms of a word), labelling (e.g., classifying words as nouns, verbs, and/or the like), chunking (e.g., grouping nouns with verbs), and/or the like. In some examples, the natural language processing model may be trained to extract the keywords from the query using another form of pattern matching, grammatical transformation, and/or the like.

As further shown in FIG. 2A, and by reference number 206, the digital assistant platform may identify an intent classification and an entity based on the keywords. The intent classification may relate to an underlying request of the query and enable the digital assistant platform to identify a target service (e.g., from the plurality of services of the services library) to enable for the user. The services may be configured to provide information relating to a data attribute, a data definition, a data location, a data derivation, a data lineage, a data cleansing rule, a data transformation rule, a data computation rule, a data aggregation rule, and/or other analytical information associated with a data element. For example, a first service may be configured to provide information about how a particular metric was derived, a second service may be configured to identify a source of a data element (e.g., a metric), a third service may be configured to determine a rule by which a data element was cleansed, transformed, computed, and/or aggregated, and so on. The digital assistant platform may identify a keyword as the intent classification based on an association between the keyword and the services of the services library. For example, the services of the services library may be indexed using respective service identifiers that can be selectively called based on keywords of the query that match and/or otherwise relate to the service identifiers.

In some implementations, the digital assistant platform may identify the entity based on an association between the keywords and data elements of the standardized data set. The entity may relate to the target data file and/or a data element of the target data file that the user is inquiring about. For example, the entity may be indicative of a type of data file (e.g., health insurance data, health insurance claims data, patient or member data, enrollment data, medical records, pharmaceutical records, payment records, billing records, and/or the like), a data element associated with a patient (e.g., a patient gender, name, member identifier, age, date of birth, and/or the like), a data element associated with a medical claim (e.g., a date of service, a healthcare provider identifier, a billed amount, a paid amount, a denied amount, and/or the like), a data element associated with a medical condition and/or treatment (e.g., a medical condition that was identified, a medical service that was performed or received, lab work that was performed, pharmaceuticals that were prescribed, and/or the like), a data element associated with a healthcare provider (e.g., a hospital identifier, a physician or doctor identifier, and/or the like), and/or the like. The digital assistant platform may compare the keywords with data elements of the standardized data set, and identify a keyword as the entity based on data elements matching the keyword.

In some implementations, such as when the keywords are insufficient to identify the intent classification and/or the entity and/or when sufficient keywords cannot be extracted from the query, the digital assistant platform may generate a subsequent request for additional information, and communicate the request for additional information to the user. In some examples, the digital assistant platform may be configured to prompt the user (e.g., via the chatbot interface) with a follow-up query that requests the user to rephrase the query, provide more information related to the intent classification of the query, provide more information related to the entity associated with the query, and/or the like. In some examples, the digital assistant platform may retrieve the follow-up query from a library of predefined follow-up queries that are indexed according to different types of information that may be needed to successfully respond to the query submitted by the user. In some examples, the digital assistant platform may use the natural language processing model to conduct a dialogue with the user (e.g., via the chatbot interface) to obtain additional information from the user. For example, the natural language processing model may be trained to generate appropriate follow-up queries for the user and monitor follow-up responses provided by the user until sufficient keywords, intent classifications, and/or entities can be identified.

In some implementations, the digital assistant platform may use a machine learning model to identify and/or classify keywords as the intent classification and/or the entity associated with the query. For example, the machine learning model may be trained to identify the intent classification based on an association between the keywords of the query and the plurality of services of the services library (e.g., via service identifiers), as described above. In some examples, the machine learning model may be trained to identify the entity based on an association between the keywords of the query and the data elements of the standardized data set, as described above. Additionally, or alternatively, the machine learning model may be trained to monitor a dialogue conducted with the user, identify a pattern in the dialogue, generate an association between the pattern and a level of satisfaction of the user, and use the association to improve upon a user experience, an efficiency of the dialogue, a relevance of responses provided to the user, an accuracy of results provided to the user, and/or the like. In some examples, such as when a user identifier is received in relation to the query, the machine learning model may be trained to generate an association that is specific to the user identifier and/or a role associated with the user identifier, and use the association to facilitate future interactions with the user.

In some implementations, the digital assistant platform may use the natural language processing model to parse natural language descriptions of keywords, intent classifications, and/or entities. For example, the natural language processing model may obtain data identifying, in natural language, a query by the user requesting analytical information in connection with a standardized data set, and may parse the data to identify the keywords, the intent classifications, the entities, and/or the like. In some examples, the natural language processing model may determine a characteristic of the analytical information requested by the user based on natural language processing of the query, which may include a description of the requested analytical information. For example, based on a query being "What are the metrics used to measure patient wait times?," the natural language processing model may determine that "metrics" and "patient wait times" are keywords of the query that are related to the analytical information requested by the user. In some examples, the natural language processing model may determine that "metrics" relate to an intent classification associated with the query, and/or determine that "patient wait times" relate to an entity associated with the query. In such cases, the natural language processing model may determine that a natural language text corresponds to a characteristic based on data relating to other analytical information, data identifying characteristics of analytical information, and/or the like.

In this way, the natural language processing model may identify characteristics associated with a query submitted by a user and/or analytical information being requested by the user, as described herein. Based on applying a rigorous and automated process associated with determining analytical information in connection with a standardized data set, the natural language processing model enables recognition and/or identification of thousands or millions of keywords, intent classifications, and/or entities for thousands or millions of queries, thereby increasing an accuracy and consistency of the analytical information provided to the user relative to requiring computing resources to be allocated for hundreds or thousands of technicians to manually provide analytical information in response to the thousands or millions of queries.

In some implementations, the digital assistant platform may use the machine learning model to identify and/or classify the requested analytical information from the query submitted by the user. In this case, the digital assistant platform may generate and/or train the machine learning model using information that includes a plurality of keywords, a plurality of intent classifications, a plurality of entities, a plurality of services of the services library, a plurality of data files and/or data elements of the standardized data set, and/or the like, to enable the machine learning model to identify the analytical information requested by the user. As an example, the machine learning model may determine that past keywords, intent classifications, and/or entities are associated with a threshold probability of being associated with particular types of analytical information. In some examples, the machine learning model may use a scoring system (e.g., with relatively high scores and/or relatively low scores) to identify and/or classify the requested analytical information.

In some implementations, the digital assistant platform may perform a data preprocessing operation when generating the machine learning model. For example, the digital assistant platform may preprocess data (e.g., data relating to keywords, intent classifications, entities, services, data files and/or data elements of the standardized data set, and/or the like) to remove non-ASCII characters, white spaces, confidential and/or sensitive data, and/or the like. In this way, the digital assistant platform may organize thousands, millions, or billions of data items for generating and/or training the machine learning model.

In some implementations, the digital assistant platform may perform a training operation when generating the machine learning model. For example, the digital assistant platform may portion data relating to keywords, intent classifications, entities, services, data files and/or data elements of the standardized data set, and/or the like into a training set (e.g., a set of data to train the machine learning model), a validation set (e.g., a set of data used to evaluate a fit of the machine learning model and/or to fine tune the machine learning model), a test set (e.g., a set of data used to evaluate a final fit of the machine learning model), and/or the like. In some examples, the digital assistant platform may preprocess and/or perform dimensionality reduction to reduce the data relating to keywords, intent classifications, entities, services, data files and/or data elements of the standardized data set, and/or the like to a minimum feature set. In some examples, the digital assistant platform may train the machine learning model on this minimum feature set, thereby reducing processing to train the machine learning model, and may apply a classification technique to the minimum feature set.

In some implementations, the digital assistant platform may use a classification technique, such as a logistic regression classification technique, a random forest classification technique, a gradient boosting machine learning (GBM) technique, and/or the like, to determine a categorical outcome (e.g., that the requested analytical information is identified, that the requested analytical information is not identified, and/or the like). Additionally, or alternatively, the digital assistant platform may use a naïve Bayesian classifier technique. In this case, the digital assistant platform may perform binary recursive partitioning to split the data of the minimum feature set into partitions and/or branches and use the partitions and/or branches to perform predictions. Based on using recursive partitioning, the digital assistant platform may reduce utilization of computing resources relative to manual, linear sorting and analysis of data items, thereby enabling use of thousands, millions, or billions of data items to train the machine learning model, which may result in a more accurate machine learning model than using fewer data items.

Additionally, or alternatively, the digital assistant platform may use a support vector machine (SVM) classifier technique to generate a non-linear boundary between data items in the training set. In this case, the non-linear boundary is used to classify test data (e.g., data relating to keywords, intent classifications, entities, services, data files and/or data elements of the standardized data set, and/or the like) into a particular class (e.g., a class indicating that the requested analytical information is identified, a class indicating that the requested analytical information is not identified, and/or the like).

Additionally, or alternatively, where the test data includes image data, video data, and/or the like, the digital assistant platform may use a computer vision technique, such as a convolutional neural network technique to assist in classifying test data (e.g., data relating to keywords, intent classifications, entities, services, data files and/or data elements of the standardized data set, and/or the like) into a particular class (e.g., a class indicating that the requested analytical information is identified, a class indicating that the requested analytical information is not identified, and/or the like). In some cases, the computer vision technique may include using an image recognition technique (e.g., an Inception framework, a ResNet framework, a Visual Geometry Group (VGG) framework, and/or the like), an object detection technique (e.g., a Single Shot Detector (SSD) framework, a You Only Look Once (YOLO) framework, and/or the like), an object in motion technique (e.g., an optical flow framework and/or the like), and/or the like.

Additionally, or alternatively, the digital assistant platform may train the machine learning model using a supervised training procedure that includes receiving input to the machine learning model from a subject matter expert, which may reduce an amount of time, an amount of processing resources, and/or the like to train the machine learning model relative to an unsupervised training procedure. In some examples, the digital assistant platform may use one or more other model training techniques, such as a neural network technique, a latent semantic indexing technique, and/or the like. For example, the digital assistant platform may perform an artificial neural network processing technique (e.g., using a two-layer feedforward neural network architecture, a three-layer feedforward neural network architecture, and/or the like) to perform pattern recognition with regard to patterns of whether data relating to keywords, intent classifications, entities, services, data files and/or data elements of the standardized data set, and/or the like described using different semantic descriptions can be used to identify the requested analytical information or not. In this case, using the artificial neural network processing technique may improve an accuracy of the machine learning model generated and/or trained by the digital assistant platform by being more robust to noisy, imprecise, or incomplete data, and by enabling the digital assistant platform to detect patterns and/or trends undetectable to human analysts or systems using less complex techniques.

In some implementations, the natural language processing model and/or the machine learning model may be provided within the digital assistant platform and trained by the digital assistant platform. In some examples, one or more components of the natural language processing model and/or the machine learning model may be provided within the client device and/or the healthcare data platform, and trained by the digital assistant platform, the client device, and/or the healthcare data platform. In some examples, another device (e.g., a server device, a cloud computing device, and/or the like) may train the natural language processing model and/or the machine learning model, and provide the trained natural language processing model and/or the machine learning model for use by the digital assistant platform, the client device, and/or the healthcare data platform. In some examples, the digital assistant platform may train the natural language processing model and/or the machine learning model for use by another device (e.g., a server device, a cloud computing device, and/or the like).

Accordingly, the digital assistant platform may use any number of artificial intelligence techniques, machine learning techniques, deep learning techniques, and/or the like to identify, determine, and/or provide analytical information relating to data files and/or data elements of a standardized data set.

As shown in FIG. 2B, and by reference number 208, a dispatcher engine of the digital assistant platform may analyze the plurality of services of the services library to identify a target service to enable. The services library may include a dictionary service (e.g., for providing information relating to an attribute of a data element), a link service (e.g., for providing reference information relating to an architecture of the healthcare data platform and/or the like), a metric service (e.g., for providing information relating to a formula, an equation, and/or a calculation used to derive a metric), a data statistics service (e.g., for providing historical data statistics), a query service (e.g., for providing historical query values), a record service (e.g., for providing information relating to a historic event), a list service (e.g., for providing a list of information relating to a client report), a profiling service (e.g., for identifying a pattern in an inbound data set), and/or another service capable of identifying, determining, and/or generating analytical information requested by the user. In some examples, the dispatcher engine may use the previously identified intent classification to search the services library for the target service. For example, if the intent classification indicates that the user is requesting information relating to a KPI of a data element, the dispatcher engine may identify the metric service as the target service to enable. In some examples, the services of the services library may be indexed using respective service identifiers that can be selectively called based on the intent classification. For example, the dispatcher engine may analyze the service identifiers for a service identifier that matches the intent classification, and identify the service indexed by the matching service identifier as the target service to enable.

As further shown in FIG. 2B, and by reference number 210, the dispatcher engine of the digital assistant platform may analyze the plurality of data elements of the standardized data set to identify the target data file associated with the query. As described above, the healthcare data platform may include a data element associated with a patient, a data element associated with a medical claim, a data element associated with a medical condition or treatment, a data element associated with a healthcare provider, and/or the like. In some examples, the dispatcher engine may use the previously identified entity of the query to search the healthcare data platform for the target data file. For example, if the entity associated with the query indicates that the user is requesting information relating to a particular patient (e.g., via a patient name), the dispatcher engine may search the data elements of the standardized data set for the patient name and identify a data file associated with the patient name as the target data file. Additionally, or alternatively, the dispatcher engine may be configured to analyze the plurality of data elements of the standardized data set to identify a target data element that is associated with the query, the entity, and/or the target data file.

As shown in FIG. 2C, and by reference number 212, the dispatcher engine may determine analytical information associated with a data element of the target data file. For example, the dispatcher engine may enable the previously identified target service to determine the analytical information requested by the user. In some examples, the dispatcher engine may be configured to call and/or retrieve the target service from the services library, and enable the target service to perform an operation on the target data file and/or data elements of the target data file to determine the analytical information. As described above, the dispatcher engine may enable a dictionary service, a link service, a metric service, a data statistics service, a query service, a record service, a list service, a profiling service, and/or another target service that is capable of determining a data attribute, a data definition, a data location, a data derivation, a data lineage, a data cleansing rule, a data transformation rule, a data computation rule, a data aggregation rule, and/or other analytical information requested by the user. For example, if the target service corresponds to a metric service and if the target data file corresponds to a KPI relating to patient wait times, the dispatcher engine may enable the metric service to determine one or more equations and/or input parameters that were used to derive the KPI for patient wait times.

As further shown in FIG. 2C, and by reference number 214, the digital assistant platform may generate a response to the query submitted by the user. For example, the digital assistant platform may generate the response based on the analytical information determined by the dispatcher engine. The digital assistant platform may generate the response as a string of characters arranged in a natural language format corresponding to the analytical information requested by the user. In some examples, the digital assistant platform may generate the response using the natural language processing model, the machine learning model, and/or another artificial intelligence model that is trained to arrange the string of characters in a format that resembles part of a dialogue (e.g., conducted via the chatbot interface of the digital assistant platform). Additionally, or alternatively, the digital assistant platform may generate the response as a table, a graph, a map, an image, an animation, a video, and/or another visual representation of the analytical information.

As further shown in FIG. 2C, and by reference number 216, the digital assistant platform may output the response to the user. For example, the digital assistant platform may communicate the response to the client device of the user (e.g., via the chatbot interface that is provided by the digital assistant platform). In some examples, the digital assistant platform may communicate the response to the user as textual data (e.g., as part of a dialogue conducted via the chatbot interface). Additionally, or alternatively, the digital assistant platform may communicate the response to the user in the form of image data, video data, audio data, and/or another format that may be supported by the client device. For example, the response may be displayed as part of a dialogue via a display of the client device, presented as an animation and/or a video via the display of the client device, dictated via a speaker of the client device, and/or the like. In some examples, the response may be communicated as an electronic file and/or record that includes the analytical information requested by the user and is transmitted to the client device of the user.

As further shown in FIG. 2C, and by reference number 218, the digital assistant platform may cause an action to be performed based on the response. In some examples, the digital assistant platform may determine, after communicating the response to the user, a satisfaction level of the user of the response. For example, the digital assistant platform may prompt the user with a survey, a questionnaire, and/or another request for feedback relating to a relevance and/or an accuracy of the response provided by the digital assistant platform, and determine the satisfaction level of the user based on the feedback. In some examples, the digital assistant platform may train the natural language processing model and/or the machine learning model based on the satisfaction level. For example, if the satisfaction level is positive for a particular response, the natural language processing model and/or the machine learning model may reinforce an association (e.g., between the keywords, the intent classification, the entity, the target service, the target data file, and/or the like) that was learned while processing the query submitted by the user. If the satisfaction level is negative, the natural language processing model and/or the machine learning model may remove and/or otherwise reduce a significance of an association that was learned while processing the query.

As indicated above, FIGS. 2A-2C are provided as one or more examples. Other examples can differ from what is described with regard to FIGS. 2A-2C.

Figure 3:
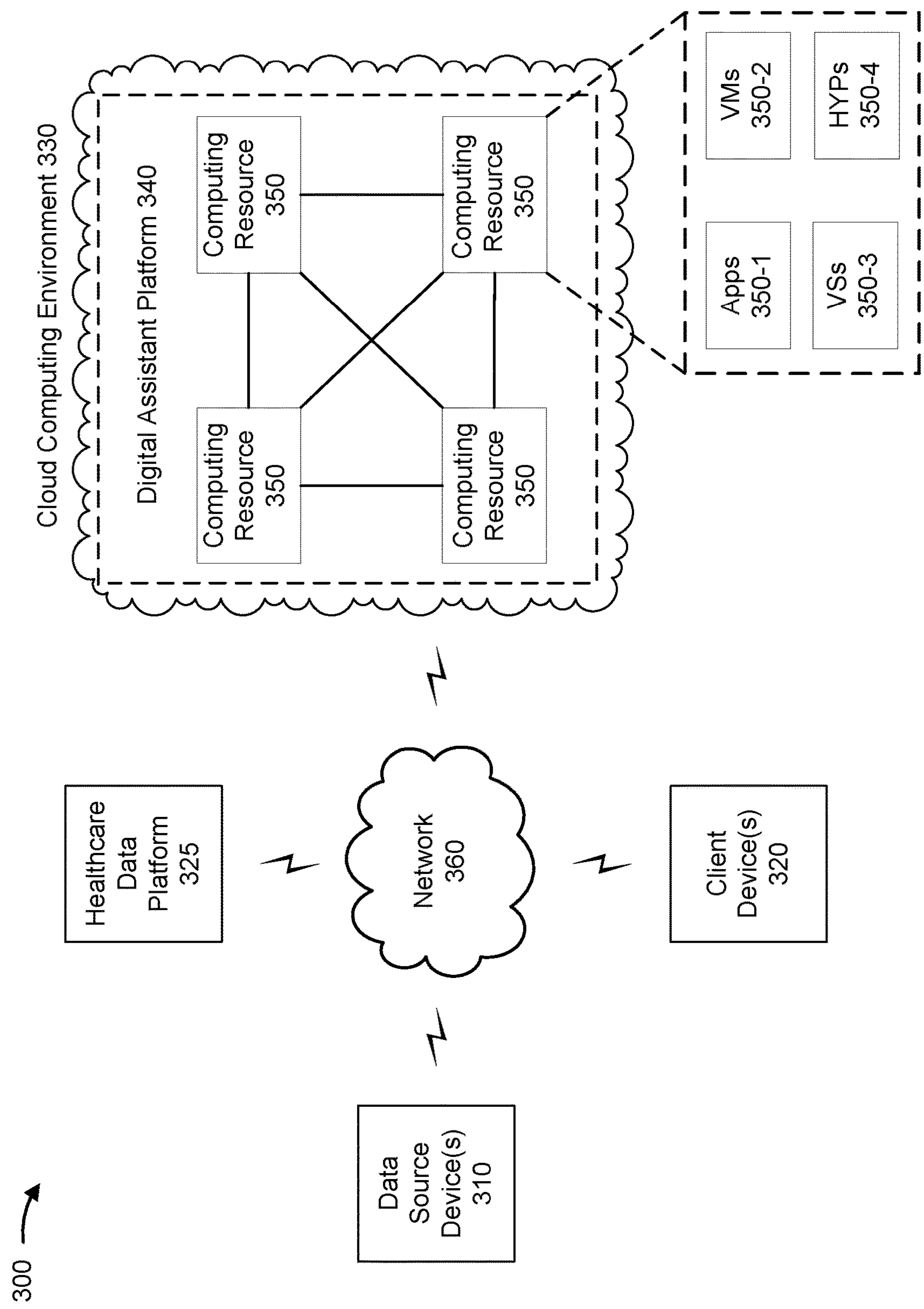
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a data source device 310, a client device 320, a healthcare data platform 325, a cloud computing environment 330, a digital assistant platform 340, a computing resource 350, and a network 360. Devices of environment 300 may interconnect via wired connections, wireless connections, or a combination of wired and wireless connections.

Data source device 310 includes one or more devices capable of sending, receiving, generating, storing, processing, communicating, and/or providing healthcare data for purposes relating to an analysis of the healthcare data. For example, data source device 310 may include a server (e.g., in a data center or a cloud computing environment), a data center (e.g., a multi-server micro data center), a workstation computer, a virtual machine (VM) provided in a cloud computing environment, or a similar type of device. In some implementations, data source device 310 may provide, to healthcare data platform 325, information related to health insurance transactions, claims, eligibility, enrollment, providers, medical records, and/or the like for analysis as described elsewhere herein. Additionally, or alternatively, data source device 310 may store information related to health insurance transactions, claims, eligibility, enrollment, providers, medical records and/or the like, as described elsewhere herein.

Client device 320 includes one or more devices capable of sending, receiving, generating, storing, processing, communicating, and/or consuming healthcare data for purposes relating to an analysis of the healthcare data. For example, client device 320 may include a server, a computer (e.g., a desktop computer, a laptop computer, a tablet computer, and/or the like), a mobile phone (e.g., a smart phone or a radiotelephone), a wearable communication device (e.g., a smart wristwatch or a pair of smart eyeglasses), or a similar type of device. In some implementations, client device 320 may receive data associated with an analysis of the healthcare data that healthcare data platform 325 has performed, and/or receive analytical information of the healthcare data that digital assistant platform 340 has determined, as described elsewhere herein. Additionally, or alternatively, client device 320 may provide information for display (e.g., information related to an analysis and/or analytical information of the healthcare data) and/or utilize the data and/or the analytical information to perform additional analyses, pay health insurance claims, deny health insurance claims, enroll members, assign providers, and/or the like, as described elsewhere herein.

Healthcare data platform 325 includes one or more devices capable of analyzing data received or obtained from a healthcare EDI. For example, healthcare data platform 325 may include a cloud server or a group of cloud servers. In some implementations, healthcare data platform 325 may be designed to be modular such that certain software components can be swapped in or out depending on a particular need. As such, healthcare data platform 325 may be easily and/or quickly reconfigured for different uses.

Cloud computing environment 330 includes an environment that delivers computing as a service, whereby shared resources, services, and/or the like may be provided to digital assistant platform 340. Cloud computing environment 330 may provide computation, software, data access, storage, and/or other services that do not require end-user knowledge of a physical location and configuration of a system and/or a device that delivers the services. As shown, cloud computing environment 330 may include digital assistant platform 340 and one or more computing resources 350.

Digital assistant platform 340 includes one or more devices capable of analyzing data received or obtained from client device 320 and/or healthcare data platform 325. For example, digital assistant platform 340 may include a cloud server or a group of cloud servers. In some implementations, digital assistant platform 340 may be designed to be modular such that certain software components can be swapped in or out depending on a particular need. As such, digital assistant platform 340 may be easily and/or quickly reconfigured for different uses.

In some implementations, as shown, digital assistant platform 340 may be hosted in cloud computing environment 330. Notably, while implementations described herein describe digital assistant platform 340 as being hosted in cloud computing environment 330, in some implementations, digital assistant platform 340 may not be cloud-based (i.e., may be implemented outside of a cloud computing environment) or may be partially cloud-based.

Computing resource 350 includes one or more personal computers, workstation computers, server devices, or other types of computation and/or communication devices. In some implementations, computing resource 350 may host digital assistant platform 340. The cloud resources may include compute instances executing in computing resource 350, storage devices provided in computing resource 350, data transfer devices provided by computing resource 350, and/or the like. In some implementations, computing resource 350 may communicate with other computing resources 350 via wired connections, wireless connections, or a combination of wired and wireless connections.

As further shown in FIG. 3, computing resource 350 may include a group of cloud resources, such as one or more applications ("APPs") 350-1, one or more virtual machines ("VMs") 350-2, virtualized storage ("VSs") 350-3, one or more hypervisors ("HYPs") 350-4, or the like.

Application 350-1 includes one or more software applications that may be provided to or accessed by client device 320. Application 350-1 may eliminate a need to install and execute the software applications on client device 320. For example, application 350-1 may include software associated with digital assistant platform 340 and/or any other software capable of being provided via cloud computing environment 330. In some implementations, one application 350-1 may send/receive information to/from one or more other applications 350-1, via virtual machine 350-2.

Virtual machine 350-2 includes a software implementation of a machine (e.g., a computer) that executes programs like a physical machine. Virtual machine 350-2 may be either a system virtual machine or a process virtual machine, depending upon use and degree of correspondence to any real machine by virtual machine 350-2. A system virtual machine may provide a complete system platform that supports execution of a complete operating system ("OS"). A process virtual machine may execute a single program, and may support a single process. In some implementations, virtual machine 350-2 may execute on behalf of a user (e.g., client device 320), and may manage infrastructure of cloud computing environment 330, such as data management, synchronization, or long-duration data transfers.

Virtualized storage 350-3 includes one or more storage systems and/or one or more devices that use virtualization techniques within the storage systems or devices of computing resource 350. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 350-4 provides hardware virtualization techniques that allow multiple operating systems (e.g., "guest operating systems") to execute concurrently on a host computer, such as computing resource 350. Hypervisor 350-4 may present a virtual operating platform to the guest operating systems, and may manage the execution of the guest operating systems. Multiple instances of a variety of operating systems may share virtualized hardware resources.

Network 360 includes one or more wired and/or wireless networks. For example, network 360 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a communications network, a private network, an ad hoc network, an intranet, the Internet, a fiber optic-based network, a cloud computing network, or the like, and/or a combination of these or other types of networks.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
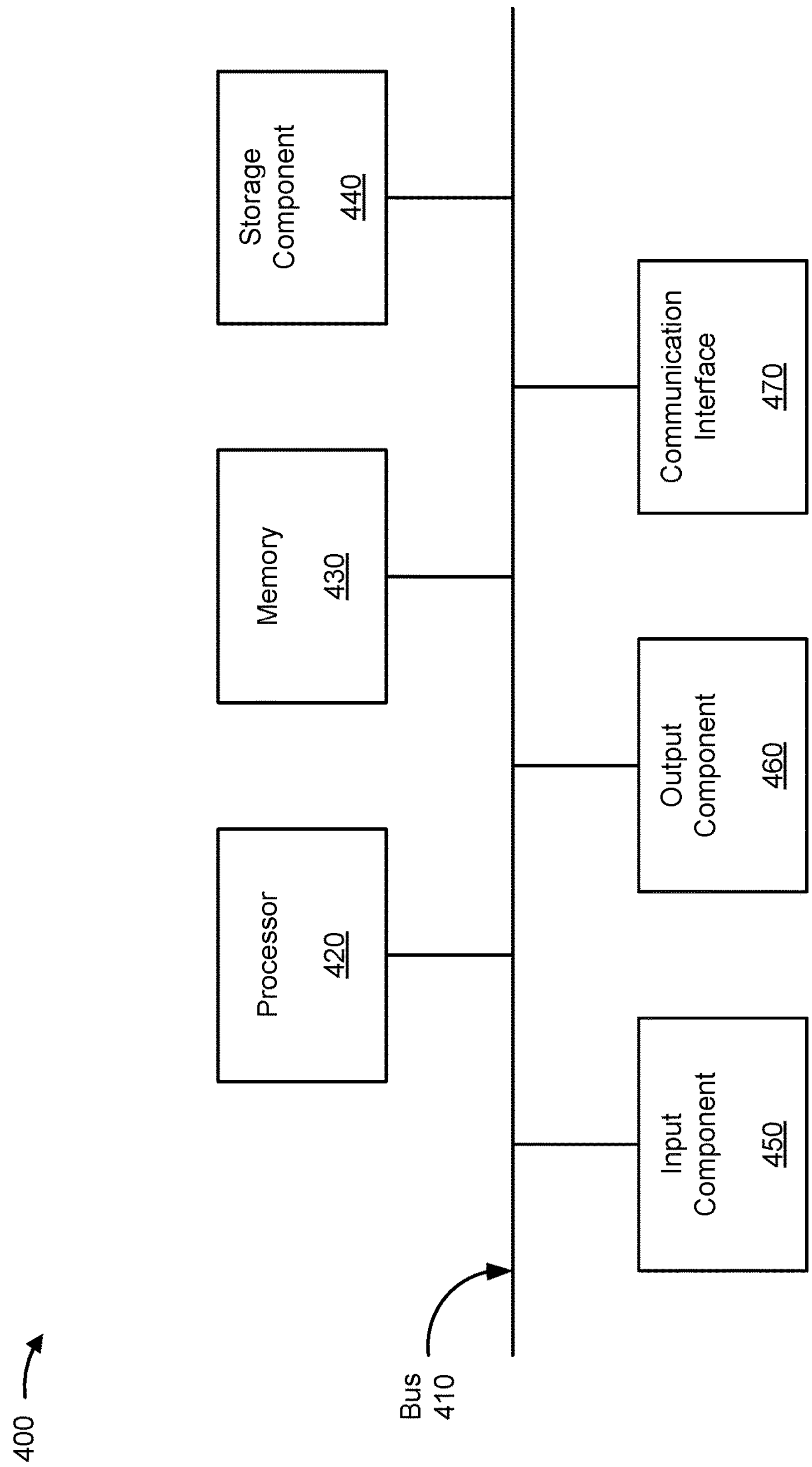
FIG. 4 is a diagram of example components of one or more devices of FIG. 3.

FIG. 4 is a diagram of example components of a device 400. Device 400 may correspond to data source device 310, client device 320, healthcare data platform 325, digital assistant platform 340, and/or computing resource 350. In some implementations, data source device 310, client device 320, healthcare data platform 325, digital assistant platform 340, and/or computing resource 350 may include one or more devices 400 and/or one or more components of device 400. As shown in FIG. 4, device 400 may include a bus 410, a processor 420, a memory 430, a storage component 440, an input component 450, an output component 460, and a communication interface 470.

Bus 410 includes a component that permits communication among the components of device 400. Processor 420 is implemented in hardware, firmware, or a combination of hardware and software. Processor 420 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 420 includes one or more processors capable of being programmed to perform a function. Memory 430 includes a random access memory (RAM), a read only memory (ROM), and/or another type of dynamic or static storage device (e.g., a flash memory, a magnetic memory, and/or an optical memory) that stores information and/or instructions for use by processor 420.

Storage component 440 stores information and/or software related to the operation and use of device 400. For example, storage component 440 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 450 includes a component that permits device 400 to receive information, such as via user input (e.g., a touch screen display, a keyboard, a keypad, a mouse, a button, a switch, and/or a microphone). Additionally, or alternatively, input component 450 may include a sensor for sensing information (e.g., a global positioning system (GPS) component, an accelerometer, a gyroscope, and/or an actuator). Output component 460 includes a component that provides output information from device 400 (e.g., a display, a speaker, and/or one or more light-emitting diodes (LEDs)).

Communication interface 470 includes a transceiver-like component (e.g., a transceiver and/or a separate receiver and transmitter) that enables device 400 to communicate with other devices, such as via a wired connection, a wireless connection, or a combination of wired and wireless connections. Communication interface 470 may permit device 400 to receive information from another device and/or provide information to another device. For example, communication interface 470 may include an Ethernet interface, an optical interface, a coaxial interface, an infrared interface, a radio frequency (RF) interface, a universal serial bus (USB) interface, a Wi-Fi interface, a cellular network interface, or the like.

Device 400 may perform one or more processes described herein. Device 400 may perform these processes based on to processor 420 executing software instructions stored by a non-transitory computer-readable medium, such as memory 430 and/or storage component 440. A computer-readable medium is defined herein as a non-transitory memory device. A memory device includes memory space within a single physical storage device or memory space spread across multiple physical storage devices.

Software instructions may be read into memory 430 and/or storage component 440 from another computer-readable medium or from another device via communication interface 470. When executed, software instructions stored in memory 430 and/or storage component 440 may cause processor 420 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 4 are provided as an example. In practice, device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
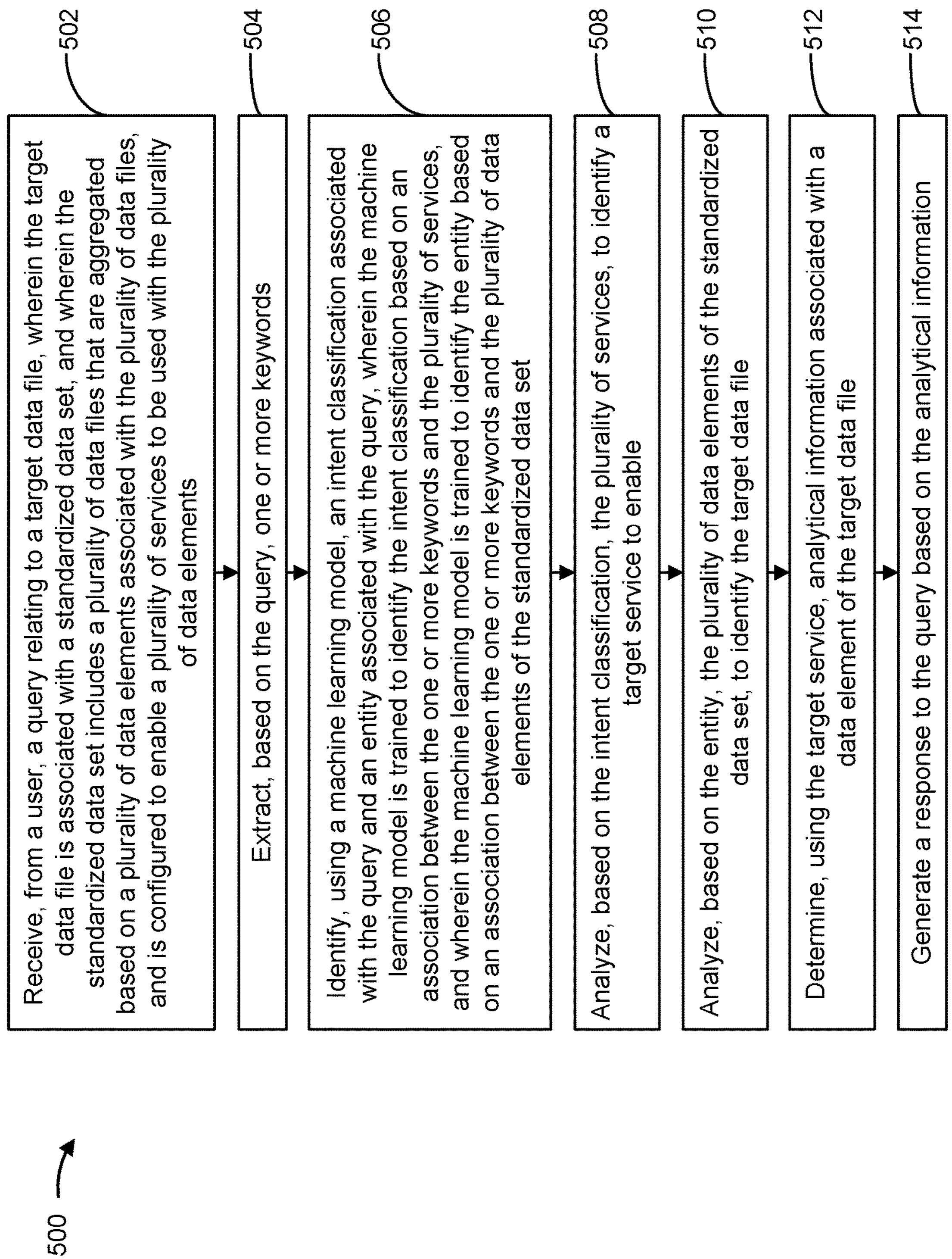
FIG. 5 is a flow chart of an example process for providing analytical information related to data elements.

FIG. 5 is a flow chart of an example process 500 for providing analytical information related to data elements. In some implementations, one or more process blocks of FIG. 5 may be performed by a digital assistant platform (e.g., digital assistant platform 340). In some implementations, one or more process blocks of FIG. 5 may be performed by another device or a group of devices separate from or including the digital assistant platform, such as a data source device (e.g., data source device 310), a client device (e.g., client device 320), a healthcare data platform (e.g., healthcare data platform 325), and/or the like.

As shown in FIG. 5, process 500 may include receiving, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements (block 502). For example, the digital assistant platform (e.g., using processor 420, memory 430, storage component 440, input component 450, output component 460, communication interface 470, and/or the like) may receive, from a user, a query relating to a target data file, as described above. In some aspects, the target data file is associated with a standardized data set. In some aspects, the standardized data set includes a plurality of data files that are aggregated based on a plurality of data elements associated with the plurality of data files, and is configured to enable a plurality of services to be used with the plurality of data elements.

As further shown in FIG. 5, process 500 may include extracting, based on the query, one or more keywords (block 504). For example, the digital assistant platform (e.g., using processor 420, memory 430, storage component 440, input component 450, output component 460, communication interface 470, and/or the like) may extract, based on the query, one or more keywords, as described above.

As further shown in FIG. 5, process 500 may include identifying, using a machine learning model, an intent classification associated with the query and an entity associated with the query, wherein the machine learning model is trained to identify the intent classification based on an association between the one or more keywords and the plurality of services, and wherein the machine learning model is trained to identify the entity based on an association between the one or more keywords and the plurality of data elements of the standardized data set (block 506). For example, the digital assistant platform (e.g., using processor 420, memory 430, storage component 440, input component 450, output component 460, communication interface 470, and/or the like) may identify, using a machine learning model, an intent classification associated with the query and an entity associated with the query, as described above. In some aspects, the machine learning model is trained to identify the intent classification based on an association between the one or more keywords and the plurality of services. In some aspects, the machine learning model is trained to identify the entity based on an association between the one or more keywords and the plurality of data elements of the standardized data set.

As further shown in FIG. 5, process 500 may include analyzing, based on the intent classification, the plurality of services, to identify a target service to enable (block 508). For example, the digital assistant platform (e.g., using processor 420, memory 430, storage component 440, input component 450, output component 460, communication interface 470, and/or the like) may analyze, based on the intent classification, the plurality of services, to identify a target service to enable, as described above.

As further shown in FIG. 5, process 500 may include analyzing, based on the entity, the plurality of data elements of the standardized data set, to identify the target data file (block 510). For example, the digital assistant platform (e.g., using processor 420, memory 430, storage component 440, input component 450, output component 460, communication interface 470, and/or the like) may analyze, based on the entity, the plurality of data elements of the standardized data set, to identify the target data file, as described above.

As further shown in FIG. 5, process 500 may include determining, using the target service, analytical information associated with a data element of the target data file (block 512). For example, the digital assistant platform (e.g., using processor 420, memory 430, storage component 440, input component 450, output component 460, communication interface 470, and/or the like) may determine, using the target service, analytical information associated with a data element of the target data file, as described above.

As further shown in FIG. 5, process 500 may include generating a response to the query based on the analytical information (block 514). For example, the digital assistant platform (e.g., using processor 420, memory 430, storage component 440, input component 450, output component 460, communication interface 470, and/or the like) may generate a response to the query based on the analytical information, as described above.

Process 500 may include additional implementations, such as any single implementation or any combination of implementations described below and/or in connection with one or more other processes described elsewhere herein.

In a first implementation, extracting the one or more keywords comprises extracting, based on the query and using a natural language processing model, the one or more keywords.

In a second implementation, alone or in combination with the first implementation, analyzing the plurality of services to identify the target service comprises analyzing the plurality of services for the target service associated with the intent classification.

In a third implementation, alone or in combination with one or more of the first and second implementations, analyzing the plurality of data elements to identify the target data file comprises analyzing the plurality of data elements for the data element associated with the entity.

In a fourth implementation, alone or in combination with one or more of the first through third implementations, determining the analytical information comprises enabling the target service to determine the analytical information based on the data element.

In a fifth implementation, alone or in combination with one or more of the first through fourth implementations, process 500 further comprises generating, based on determining that one or more of the intent classification or the entity cannot be identified based on the query, a request for additional information, and communicating the request for additional information to the user.

In a sixth implementation, alone or in combination with one or more of the first through fifth implementations, process 500 further comprises communicating the response to the query to the user, determining, after communicating the response to the user, a satisfaction level of the user of the response, and training the machine learning model based on the satisfaction level.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
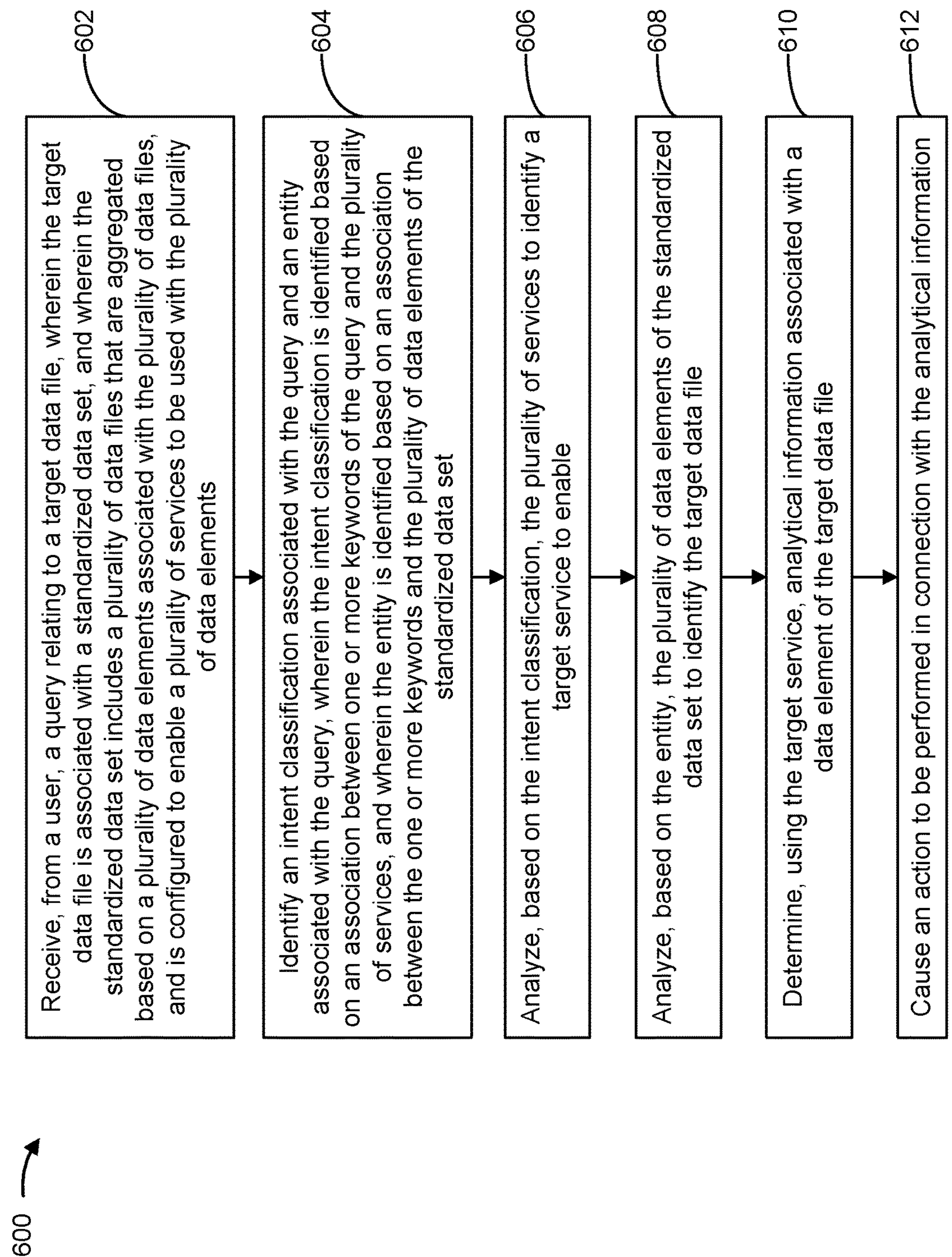
FIG. 6 is a flow chart of another example process for providing analytical information related to data elements.

FIG. 6 is a flow chart of another example process 600 for providing analytical information related to data elements. In some implementations, one or more process blocks of FIG. 6 may be performed by digital assistant platform (e.g., digital assistant platform 340). In some implementations, one or more process blocks of FIG. 6 may be performed by another device or a group of devices separate from or including the digital assistant platform, such as a data source device (e.g., data source device 310), a client device (e.g., client device 320), a healthcare data platform (e.g., healthcare data platform 325), and/or the like.

As shown in FIG. 6, process 600 may include receiving, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements (block 602). For example, the digital assistant platform (e.g., using processor 420, memory 430, storage component 440, input component 450, output component 460, communication interface 470, and/or the like) may receive, from a user, a query relating to a target data file, as described above. In some aspects, the target data file is associated with a standardized data set. In some aspects, the standardized data set includes a plurality of data files that are aggregated based on a plurality of data elements associated with the plurality of data files, and is configured to enable a plurality of services to be used with the plurality of data elements.

As further shown in FIG. 6, process 600 may include identifying an intent classification associated with the query and an entity associated with the query, wherein the intent classification is identified based on an association between one or more keywords of the query and the plurality of services, and wherein the entity is identified based on an association between the one or more keywords and the plurality of data elements of the standardized data set (block 604). For example, the digital assistant platform (e.g., using processor 420, memory 430, storage component 440, input component 450, output component 460, communication interface 470, and/or the like) may identify an intent classification associated with the query and an entity associated with the query, as described above. In some aspects, the intent classification is identified based on an association between one or more keywords of the query and the plurality of services. In some aspects, the entity is identified based on an association between the one or more keywords and the plurality of data elements of the standardized data set.

As further shown in FIG. 6, process 600 may include analyzing, based on the intent classification, the plurality of services to identify a target service to enable (block 606). For example, the digital assistant platform (e.g., using processor 420, memory 430, storage component 440, input component 450, output component 460, communication interface 470, and/or the like) may analyze, based on the intent classification, the plurality of services to identify a target service to enable, as described above.

As further shown in FIG. 6, process 600 may include analyzing, based on the entity, the plurality of data elements of the standardized data set to identify the target data file (block 608). For example, the digital assistant platform (e.g., using processor 420, memory 430, storage component 440, input component 450, output component 460, communication interface 470, and/or the like) may analyze, based on the entity, the plurality of data elements of the standardized data set to identify the target data file, as described above.

As further shown in FIG. 6, process 600 may include determining, using the target service, analytical information associated with a data element of the target data file (block 610). For example, the digital assistant platform (e.g., using processor 420, memory 430, storage component 440, input component 450, output component 460, communication interface 470, and/or the like) may determine, using the target service, analytical information associated with a data element of the target data file, as described above.

As further shown in FIG. 6, process 600 may include causing an action to be performed in connection with the analytical information (block 612). For example, the digital assistant platform (e.g., using processor 420, memory 430, storage component 440, input component 450, output component 460, communication interface 470, and/or the like) may cause an action to be performed in connection with the analytical information, as described above.

Process 600 may include additional implementations, such as any single implementation or any combination of implementations described below and/or in connection with one or more other processes described elsewhere herein.

In a first implementation, receiving the query comprises receiving the query as one or more of textual data or audio data from the user. In some implementations, the query corresponds to a string of characters arranged in a natural language format.

In a second implementation, alone or in combination with the first implementation, identifying the intent classification and the entity comprises identifying, using a machine learning model, the intent classification associated with the query and the entity associated with the query. In some implementations, the machine learning model is trained to identify the intent classification based on an association between the one or more keywords and the plurality of services. In some implementations, the machine learning model is trained to identify the entity based on an association between the one or more keywords and the plurality of data elements of the standardized data set.

In a third implementation, alone or in combination with one or more of the first and second implementations, determining the analytical information comprises enabling the target service to determine the analytical information based on the data element. In some implementations, the target service is configured to determine one or more of a data attribute, a data definition, a data location, a data derivation, a data lineage, a data cleansing rule, a data transformation rule, a data computation rule, or a data aggregation rule associated with the data element.

In a fourth implementation, alone or in combination with one or more of the first through third implementations, causing the action to be performed comprises generating a response to the query based on the analytical information. In some implementations, the response includes a string of characters arranged in a natural language format. In some implementations, the string of characters corresponds to the analytical information associated with the data element of the target data file. In some implementations, the response is communicated to the user as one or more of textual data, image data, video data, or audio data.

In a fifth implementation, alone or in combination with one or more of the first through fourth implementations, process 600 further comprises extracting, based on the query and using a natural language processing model, the one or more keywords.

In a sixth implementation, alone or in combination with one or more of the first through fifth implementations, process 600 further comprises receiving, from the user, a topic selection from a plurality of topics. In some implementations, the plurality of topics correspond to aggregations of the plurality of data files of the standardized data set. In some implementations, the topic selection relates to an aggregation associated with the target data file.

In a seventh implementation, alone or in combination with one or more of the first through sixth implementations, process 600 further comprises authenticating the user based on a user identifier associated with the query, the user identifier including information identifying a role of the user, determining an access level for the user based on the role of the user, and filtering the analytical information based on the access level.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
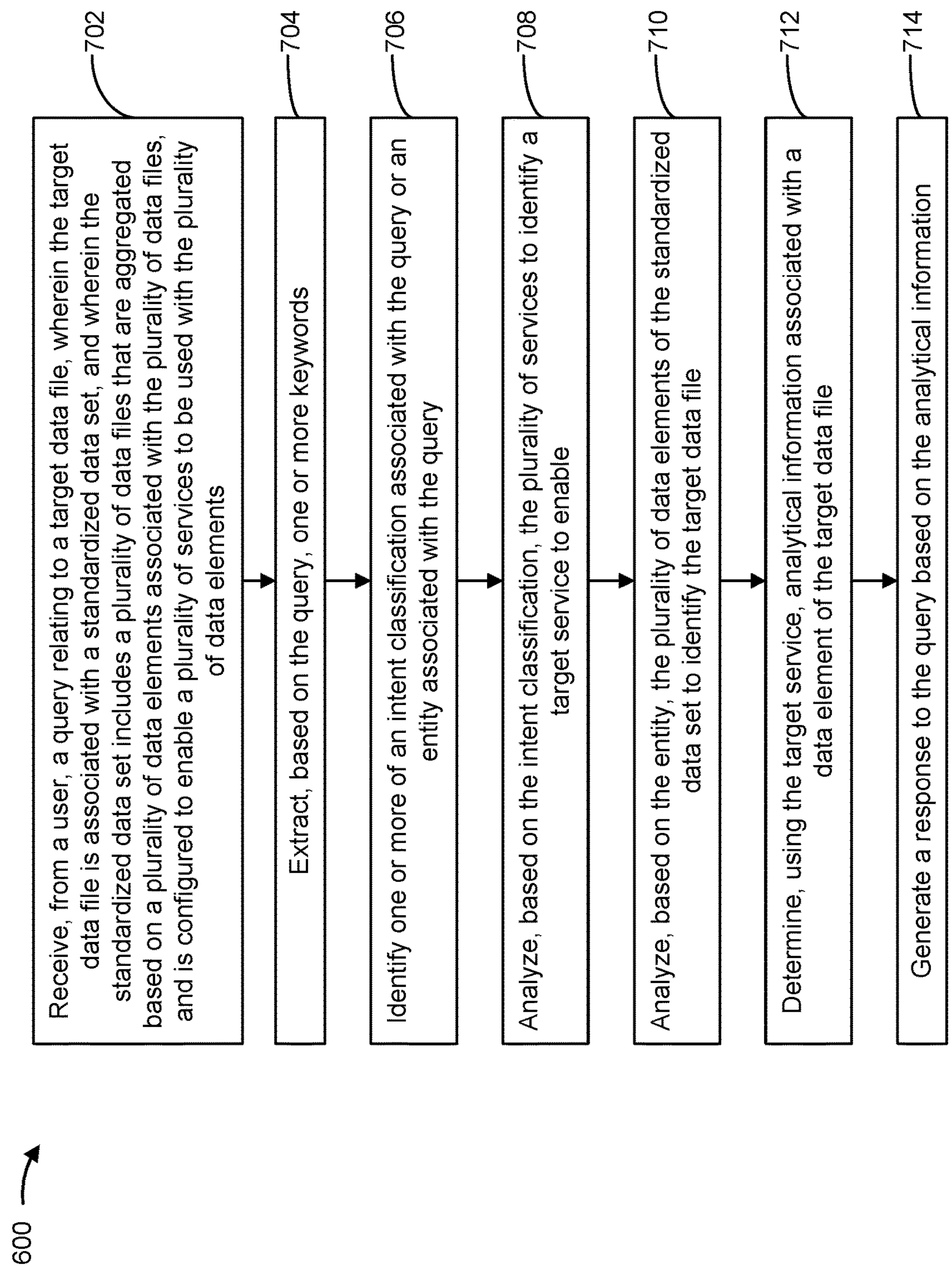
FIG. 7 is a flow chart of yet another example process for providing analytical information related to data elements.

FIG. 7 is a flow chart of yet another example process 700 for providing analytical information related to data elements. In some implementations, one or more process blocks of FIG. 7 may be performed by digital assistant platform (e.g., digital assistant platform 340). In some implementations, one or more process blocks of FIG. 7 may be performed by another device or a group of devices separate from or including the digital assistant platform, such as a data source device (e.g., data source device 310), a client device (e.g., client device 320), a healthcare data platform (e.g., healthcare data platform 325), and/or the like.

As shown in FIG. 7, process 700 may include receiving, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements (block 702). For example, the digital assistant platform (e.g., using processor 420, memory 430, storage component 440, input component 450, output component 460, communication interface 470, and/or the like) may receive, from a user, a query relating to a target data file, as described above. In some aspects, the target data file is associated with a standardized data set. In some aspects, the standardized data set includes a plurality of data files that are aggregated based on a plurality of data elements associated with the plurality of data files, and is configured to enable a plurality of services to be used with the plurality of data elements.

As further shown in FIG. 7, process 700 may include extracting, based on the query, one or more keywords (block 704). For example, the digital assistant platform (e.g., using processor 420, memory 430, storage component 440, input component 450, output component 460, communication interface 470, and/or the like) may extract, based on the query, one or more keywords, as described above.

As further shown in FIG. 7, process 700 may include identifying one or more of an intent classification associated with the query or an entity associated with the query (block 706). For example, the digital assistant platform (e.g., using processor 420, memory 430, storage component 440, input component 450, output component 460, communication interface 470, and/or the like) may identify one or more of an intent classification associated with the query or an entity associated with the query, as described above.

As further shown in FIG. 7, process 700 may include analyzing, based on the intent classification, the plurality of services to identify a target service to enable (block 708). For example, the digital assistant platform (e.g., using processor 420, memory 430, storage component 440, input component 450, output component 460, communication interface 470, and/or the like) may analyze, based on the intent classification, the plurality of services to identify a target service to enable, as described above.

As further shown in FIG. 7, process 700 may include analyzing, based on the entity, the plurality of data elements of the standardized data set to identify the target data file (block 710). For example, the digital assistant platform (e.g., using processor 420, memory 430, storage component 440, input component 450, output component 460, communication interface 470, and/or the like) may analyze, based on the entity, the plurality of data elements of the standardized data set to identify the target data file, as described above.

As further shown in FIG. 7, process 700 may include determining, using the target service, analytical information associated with a data element of the target data file (block 712). For example, the digital assistant platform (e.g., using processor 420, memory 430, storage component 440, input component 450, output component 460, communication interface 470, and/or the like) may determine, using the target service, analytical information associated with a data element of the target data file, as described above.

As further shown in FIG. 7, process 700 may include generating a response to the query based on the analytical information (block 714). For example, the digital assistant platform (e.g., using processor 420, memory 430, storage component 440, input component 450, output component 460, communication interface 470, and/or the like) may generate a response to the query based on the analytical information, as described above.

Process 700 may include additional implementations, such as any single implementation or any combination of implementations described below and/or in connection with one or more other processes described elsewhere herein.

In a first implementation, identifying one or more of the intent classification or the entity comprises identifying, using a machine learning model, one or more of the intent classification associated with the query or the entity associated with the query. In some implementations, the machine learning model is trained to identify one or more of the intent classification or the entity based on one or more of an association between the one or more keywords, the plurality of services, or an association between the one or more keywords and the plurality of data elements of the standardized data set.

In a second implementation, alone or in combination with the first implementation, determining the analytical information comprises enabling the target service to determine the analytical information based on the data element. In some implementations, the target service is configured to determine one or more of a data attribute, a data definition, a data location, a data derivation, a data lineage, a data cleansing rule, a data transformation rule, a data computation rule, or a data aggregation rule associated with the data element.

In a third implementation, alone or in combination with one or more of the first and second implementations, process 700 further comprises receiving, from the user, a topic selection from a plurality of topics. In some implementations, the plurality of topics corresponds to aggregations of the plurality of data files of the standardized data set. In some implementations, the topic selection relates to an aggregation associated with the target data file.

In a fourth implementation, alone or in combination with one or more of the first through third implementations, process 700 further comprises communicating the response to the query to the user, determining, after communicating the response to the user, a satisfaction level of the user of the response, and training a machine learning model based on the satisfaction level. In some implementations, the machine learning model is trained to identify one or more of the intent classification or the entity based on one or more of an association between the one or more keywords, the plurality of services, or an association between the one or more keywords and the plurality of data elements of the standardized data set.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Additionally, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, and/or the like), and may be used interchangeably with "one or more." Where only one item is intended, the term "only one" or similar language is used. Additionally, as used herein, the terms "has," "have," "having," or the like are intended to be open-ended terms. Further, the phrase "based on" is intended to refer to "based, at least in part, on" unless explicitly stated otherwise.

What is claimed is:

1. A method, comprising:

receiving, by a device and from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements, wherein the plurality of data elements are grouped based on mapping one or more attribute identifiers associated with the plurality of data elements to one or more repositories for which the plurality of data elements may be used to perform one or more analyses;

extracting, by the device and based on the query, one or more keywords;

identifying, by the device and using a machine learning model, an intent classification associated with the query and an entity associated with the query, wherein the machine learning model is trained to identify the intent classification based on an association between the one or more keywords and the plurality of services, and wherein the machine learning model is trained to identify the entity based on an association between the one or more keywords and the plurality of data elements;

analyzing, by the device and based on the intent classification, the plurality of services, to identify a target service to enable;

enabling, by the device, the target service;

analyzing, by the device and based on the entity, the plurality of data elements, to identify the target data file;

determining, by the device and using the enabled target service, analytical information associated with a data element of the target data file; and generating, by the device, a response to the query based on the analytical information.

2. The method of claim 1, wherein extracting the one or more keywords comprises:

extracting, based on the query and using a natural language processing model, the one or more keywords, wherein the natural language processing model is trained to use one or more of tokenizing, filtering, stemming, lemmatizing, labelling, or chunking to extract the one or more keywords from a string of characters of the query.

3. The method of claim 1, wherein analyzing the plurality of services to identify the target service to enable comprises:

analyzing the plurality of services for the target service associated with the intent classification, wherein the plurality of services provides information relating to one or more of a data attribute, a data definition, a data location, a data derivation, a data lineage, a data cleansing rule, a data transformation rule, a data computation rule, or a data aggregation rule.

4. The method of claim 1, wherein analyzing the plurality of data elements to identify the target data file comprises:

analyzing the plurality of data elements for the data element associated with the entity, wherein the plurality of data elements includes information relating to one or more of a patient, a medical condition, a medical treatment, a medical claim, or a healthcare provider.

5. The method of claim 1, further comprising:

generating, based on determining that one or more of the intent classification or the entity cannot be identified based on the query, a request for additional information; and communicating the request for additional information to the user.

6. The method of claim 1, further comprising:

communicating the response to the query to the user;

determining, after communicating the response to the user, a satisfaction level of the user of the response; and training the machine learning model based on the satisfaction level.

7. The method of claim 1, wherein the plurality of data elements are associated with the one or more attribute identifiers based on a type of data the machine learning model predicts will be present within the plurality of data files.

8. A device, comprising:

one or more memories at least partially implemented in hardware; and one or more processors, at least partially implemented in the hardware, communicatively coupled to the one or more memories, configured to:

receive, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements, wherein the plurality of data elements are grouped based on mapping one or more attribute identifiers associated with the plurality of data elements to one or more repositories for which the plurality of data elements may be used to perform one or more analyses;

identify an intent classification associated with the query and an entity associated with the query, wherein the intent classification is identified based on an association between one or more keywords of the query and the plurality of services, and wherein the entity is identified based on an association between the one or more keywords and the plurality of data elements;

analyze, based on the intent classification, the plurality of services to identify a target service to enable;

enable the target service;

analyze, based on the entity, the plurality of data elements to identify the target data file;

determine, using the enabled target service, analytical information associated with a data element of the target data file; and cause an action to be performed in connection with the analytical information.

9. The device of claim 8, wherein the one or more processors, when receiving the query, are configured to:

receive the query as one or more of textual data or audio data from the user, wherein the query corresponds to a string of characters arranged in a natural language format.

10. The device of claim 8, wherein the one or more processors, when identifying the intent classification and the entity, are configured to:

identify, using a machine learning model, the intent classification associated with the query and the entity associated with the query, wherein the machine learning model is trained to identify the intent classification based on an association between the one or more keywords and the plurality of services, and wherein the machine learning model is trained to identify the entity based on an association between the one or more keywords and the plurality of data elements.

11. The device of claim 8, wherein the enabled target service is configured to determine one or more of a data attribute, a data definition, a data location, a data derivation, a data lineage, a data cleansing rule, a data transformation rule, a data computation rule, or a data aggregation rule associated with the data element.

12. The device of claim 8, wherein the one or more processors, when causing the action to be performed, are configured to:

generate a response to the query based on the analytical information, wherein the response includes a string of characters arranged in a natural language format, wherein the string of characters corresponds to the analytical information associated with the data element of the target data file, and wherein the response is communicated to the user as one or more of textual data, image data, video data, or audio data.

13. The device of claim 8, wherein the one or more processors are further configured to:

extract, based on the query and using a natural language processing model, the one or more keywords, wherein the natural language processing model is trained to use one or more of tokenizing, filtering, stemming, lemmatizing, labelling, or chunking to extract the one or more keywords from a string of characters of the query.

14. The device of claim 8, wherein the one or more processors are further configured to:

receive, from the user, a topic selection from a plurality of topics, wherein the plurality of topics correspond to aggregations of the plurality of data files of the standardized data set, and wherein the topic selection relates to an aggregation associated with the target data file.

15. The device of claim 8, wherein the one or more processors are further configured to:

authenticate the user based on a user identifier associated with the query, wherein the user identifier includes information identifying a role of the user; determine an access level for the user based on the role of the user; and filter the analytical information based on the access level.

16. A non-transitory computer-readable medium storing instructions, the instructions comprising:

one or more instructions that, when executed by one or more processors at least partially implemented in hardware, cause the one or more processors to:

receive, from a user, a query relating to a target data file, wherein the target data file is associated with a standardized data set, and wherein the standardized data set includes a plurality of data files that are aggregated based on a plurality of data elements associated with the plurality of data files, and is configured to enable a plurality of services to be used with the plurality of data elements, wherein the plurality of data elements are grouped based on mapping one or more attribute identifiers associated with the plurality of data elements to one or more repositories for which the plurality of data elements may be used to perform one or more analyses;

extract, based on the query, one or more keywords;

identify one or more of an intent classification associated with the query or an entity associated with the query;

analyze, based on the intent classification, the plurality of services to identify a target service to enable;

enable the target service;

analyze, based on the entity, the plurality of data elements to identify the target data file;

determine, using the enabled target service, analytical information associated with a data element of the target data file; and generate a response to the query based on the analytical information.

17. The non-transitory computer-readable medium of claim 16, wherein the one or more instructions, that cause the one or more processors to identify one or more of the intent classification or the entity, cause the one or more processors to:

identify, using a machine learning model, one or more of the intent classification associated with the query or the entity associated with the query, wherein the machine learning model is trained to identify one or more of the intent classification or the entity based on one or more of an association between the one or more keywords and the plurality of services, or an association between the one or more keywords and the plurality of data elements of the standardized data set.

18. The non-transitory computer-readable medium of claim 16, wherein the enabled target service is configured to determine one or more of a data attribute, a data definition, a data location, a data derivation, a data lineage, a data cleansing rule, a data transformation rule, a data computation rule, or a data aggregation rule associated with the data element.

19. The non-transitory computer-readable medium of claim 16, wherein the one or more instructions, when executed by the one or more processors, further cause the one or more processors to:

receive, from the user, a topic selection from a plurality of topics, wherein the plurality of topics corresponds to aggregations of the plurality of data files of the standardized data set, and wherein the topic selection relates to an aggregation associated with the target data file.

20. The non-transitory computer-readable medium of claim 16, wherein the one or more instructions, when executed by the one or more processors, further cause the one or more processors to:

communicate the response to the query to the user;

determine, after communicating the response to the user, a satisfaction level of the user of the response; and train a machine learning model based on the satisfaction level, wherein the machine learning model is trained to identify one or more of the intent classification or the entity based on one or more of an association between the one or more keywords and the plurality of services, or an association between the one or more keywords and the plurality of data elements.

* * * * *